(12) United States Patent
Cohen et al.

(10) Patent No.: US 8,048,884 B2
(45) Date of Patent: Nov. 1, 2011

(54) SUBSTITUTED PIPERAZINYL PYRAZINES AND PYRIDINES AS 5-$HT_7$ RECEPTOR ANTAGONISTS

(75) Inventors: Michael Philip Cohen, Indianapolis, IN (US); Sarah Lynne Hellman, Indianapolis, IN (US); Sean Patrick Hollinshead, Indianapolis, IN (US); Sandra Ann Filla, Franklin, IN (US); Michael Wade Tidwell, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 248 days.

(21) Appl. No.: 12/447,546

(22) PCT Filed: Aug. 19, 2008

(86) PCT No.: PCT/US2008/073543
§ 371 (c)(1),
(2), (4) Date: Apr. 28, 2009

(87) PCT Pub. No.: WO2009/029439
PCT Pub. Date: Mar. 5, 2009

(65) Prior Publication Data
US 2010/0075976 A1    Mar. 25, 2010

Related U.S. Application Data

(60) Provisional application No. 60/968,344, filed on Aug. 28, 2007, provisional application No. 61/048,752, filed on Apr. 29, 2008.

(51) Int. Cl.
| | |
|---|---|
| A01N 43/58 | (2006.01) |
| A01N 43/60 | (2006.01) |
| A61K 31/50 | (2006.01) |
| A61K 31/495 | (2006.01) |
| A61K 31/497 | (2006.01) |

(52) U.S. Cl. .............. 514/247; 514/248; 514/252.1; 514/252.12; 514/252.13

(58) Field of Classification Search .............. 514/247, 514/248, 252.1, 252.12, 252.13
See application file for complete search history.

(56) References Cited

FOREIGN PATENT DOCUMENTS

| | | |
|---|---|---|
| EP | 1254905 A1 | 11/2002 |
| WO | WO 2004/069794 A3 | 8/2004 |
| WO | WO2004/067703 A2 | 8/2007 |

OTHER PUBLICATIONS

Leopoldo, "Serotonin(7)receptors(5-HT(7)Rs) and their Ligands", *Curr. Med. Chem.*, vol. 11, pp. 629-661, (2004).

*Primary Examiner* — Yong Chong
(74) *Attorney, Agent, or Firm* — R. Craig Tucker

(57) ABSTRACT

The present invention provides selective 5-$HT_7$ receptor antagonist compounds of Formula I and their use in the treatment of migraine:

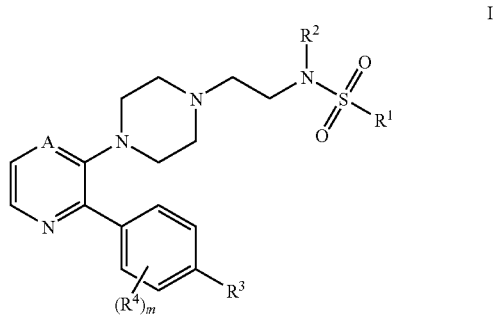

where A is —C(H)= or —N=; m is 0, 1 or 2; $R^1$ is optionally substituted phenyl, optionally substituted pyrazol-4-yl; optionally substituted imidazolyl, optionally substituted pyridyl, or thienyl; $R^2$ is hydrogen or methyl; and $R^3$ and $R^4$ are as defined herein.

13 Claims, No Drawings

SUBSTITUTED PIPERAZINYL PYRAZINES AND PYRIDINES AS 5-HT$_7$ RECEPTOR ANTAGONISTS

This U.S. National Stage Application of International Application PCT/US2008/073543 in Aug. 19, 2008, claims priority to U.S. Provisional Application Ser. No. 60/968,344, filed Aug. 28, 2007 and U.S. Provisional Application Ser. No. 61/048,752 filed Apr. 29, 2008.

The neurotransmitter serotonin (5-hydroxytryptamine, 5-HT) has a rich pharmacology arising from a heterogeneous population of at least 14 distinct receptors. Each receptor has a distinct, though often overlapping distribution throughout the body and a unique serotonin binding site leading to different affinities for serotonin and different physiological responses to interaction with serotonin. The 5-HT$_7$ receptor has been shown to have important functional roles in thermoregulation, circadian rhythm, learning and memory, hippocampal signaling, and sleep. The 5-HT$_7$ receptor has also been linked to various neurological disorders including migraine and anxiety, as well as to persistent pain, more specifically inflammatory pain and neuropathic pain.

High affinity 5-HT$_7$ receptor antagonists would provide useful therapeutics for the treatment of the above mentioned 5-HT$_7$ receptor-associated disorders including migraine, and persistent pain, particularly, inflammatory and neuropathic pain. High affinity 5-HT$_7$ receptor antagonists that are also selective for the 5-HT$_7$ receptor, would provide such therapeutic benefit without the undesirable adverse events associated with modulation of the other serotonergic receptor subclasses, such as 5-HT$_{1A}$, 5-HT$_{1B}$ and 5-HT$_{1D}$. Achieving selectivity for the 5-HT$_7$ receptor has proven difficult in designing 5-HT$_7$ antagonists. 5-HT$_{1A}$ receptor agonists have been associated with serotonin syndrome. 5-HT$_{1B}$ and 5-HT$_{1D}$ receptor agonists have been associated with adverse events such as chest pain.

Leopoldo, M. (2004) Serotonin (7) receptors (5-HT(7)Rs) and their ligands. Curr. Med. Chem. 11, 629-661, describes various prior approaches to obtaining 5-HT$_7$ receptor ligands. WO 2004/067703 discloses certain compounds as 5-HT$_7$ antagonists, some of which are 2-(4-alkyl-piperazin-1-yl)-3-(4-heteroaryl-phenyl)-pyridine compounds.

The present invention provides novel potent 5-HT$_7$ receptor antagonists. Certain compounds of the present invention are selective for the 5-HT$_7$ receptor compared with other serotonin receptors.

The present invention provides 5-HT$_7$ receptor antagonist compounds of Formula I:

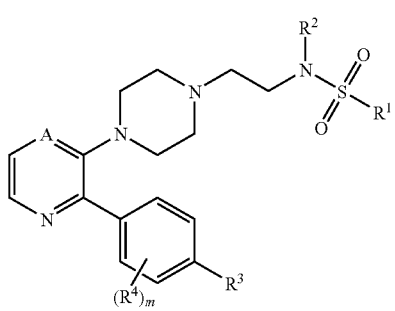

where:
A is —C(H)═ or —N═,
R$^1$ is selected from the group consisting of phenyl optionally substituted with methoxy or 1 to 3 independently selected fluoro or chloro substituents; pyrazol-4-yl optionally substituted with 1 to 3 methyl or ethyl groups; imidazolyl optionally substituted with 1 or 2 methyl or ethyl groups; pyridyl optionally substituted with fluoro or chloro; and thienyl;
R$^2$ is hydrogen or methyl;
m is 0, 1, or 2;
R$^3$ is selected from the group consisting of hydrogen, fluoro, chloro, hydroxy, methoxy, hydroxymethyl, cyanomethyl, methoxymethyl, acetyl, methylcarbonylamino, methylcarbonylaminomethyl, pyrazol-1-ylmethyl, and triazolylmethyl, provided that when R$^3$ is hydrogen, m is not 0;
each R$^4$ is independently selected from the group consisting of fluoro, chloro, methyl, and methoxy; or alternatively, two R$^4$ groups together with the phenyl to which they are attached join to form an indol-4-yl group;
or a pharmaceutically acceptable salt thereof.

The present invention also provides pharmaceutical compositions comprising a compound of Formula I, or a pharmaceutically acceptable salt thereof, in association with a pharmaceutically acceptable carrier, diluent, or excipient.

In another aspect of the present invention, there is provided one or more compounds of Formula I, or pharmaceutically acceptable salt(s) thereof for use in therapy. This aspect includes one or more compounds of Formula I, or pharmaceutically acceptable salt(s) thereof for use as a pharmaceutical. Likewise, this aspect of the invention provides one or more compounds of Formula I, or pharmaceutically acceptable salt(s) thereof for use in the treatment of migraine in mammals, particularly humans, the prophylactic treatment of migraine in mammals, particularly humans, or the treatment of persistent pain, particularly inflammatory or neuropathic pain, in mammals, particularly humans.

One embodiment of this aspect of the invention provides a method for treating migraine in mammals comprising administering to a mammal in need of such treatment an effective amount of a compound of Formula I, or a pharmaceutically acceptable salt thereof.

Another embodiment of this aspect of the invention provides a method for the prophylactic treatment of migraine in mammals comprising administering to a mammal in need of such treatment, that is to say a mammal that is susceptible to migraine, an effective amount of a compound of Formula I, or a pharmaceutically acceptable salt thereof.

Yet another embodiment of this aspect of the invention provides a method for the treatment of persistent pain in mammals comprising administering to a mammal in need of such treatment an effective amount of a compound of Formula I, or a pharmaceutically acceptable salt thereof. Particular embodiments of this are the treatment of inflammatory pain and/or neuropathic pain.

Yet another embodiment of this aspect of the invention provides a method for treating anxiety in mammals comprising administering to a mammal in need of such treatment an effective amount of a compound of Formula I, or a pharmaceutically acceptable salt thereof.

In preferred embodiments of the above methods of treatment utilizing the compounds of Formula I, or pharmaceutically acceptable salts thereof, the mammal is a human.

In another aspect of the present invention, there is provided the use of a compound of Formula I, or pharmaceutically acceptable salt thereof, in the manufacture of a medicament for the treatment and/or the prophylactic treatment of migraine.

Another aspect of the invention provides a formulation comprising a compound of the present invention, or pharmaceutically acceptable salt thereof, and methods of using a compound of the present invention, or pharmaceutically acceptable salt thereof, for treating or preventing migraine.

In another aspect of the present invention, there is provided the use of a compound of Formula I, or pharmaceutically acceptable salt thereof, in the manufacture of a medicament for the treatment of persistent pain, particularly inflammatory and/or neuropathic pain.

In another aspect of the present invention, there is provided the use of a compound of Formula I, or pharmaceutically acceptable salt thereof, in the manufacture of a medicament for the treatment of anxiety.

Additionally, the present invention provides a pharmaceutical formulation adapted for the treatment of migraine and/or for the prophylactic treatment of migraine, comprising a compound of Formula I, or a pharmaceutically acceptable salt thereof, in association with a pharmaceutically acceptable carrier, diluent or excipient.

Likewise, the present invention provides a pharmaceutical formulation adapted for the treatment of persistent pain, particularly inflammatory and/or neuropathic pain, comprising a compound of Formula I, or a pharmaceutically acceptable salt thereof, in association with a pharmaceutically acceptable carrier, diluent or excipient.

Additionally, the present invention provides a pharmaceutical formulation adapted for the treatment of anxiety comprising a compound of Formula I, or a pharmaceutically acceptable salt thereof, in association with a pharmaceutically acceptable carrier, diluent or excipient.

The general chemical terms used throughout have their usual meanings. For example, the term "amino protecting group" as used in this specification refers to a substituent commonly employed to block or protect an amino functionality while reacting other functional groups on the compound. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", $3^{rd}$ edition, John Wiley and Sons, New York, N.Y., 1999, chapter 7, hereafter referred to as "*Greene*".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of antagonizing 5-HT$_7$ receptors and/or eliciting a given pharmacological effect.

The term "suitable solvent" refers to any solvent, or mixture of solvents that sufficiently solubilizes the reactants to afford a medium within which to effect the desired reaction and that does not interfere with the desired reaction.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see, e.g., P. Stahl, et al., Handbook of Pharmaceutical Salts Properties, Selection and Use, (VCHA/Wiley-VCH, 2002); Berge, S. M, Bighley, L. D., and Monkhouse, D. C., *J. Pharm. Sci.*, 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio.

Abbreviations used herein are defined as follows:

"Brine" means a saturated aqueous sodium chloride solution.

"EtOAc" means ethylacetate.

"LC MS(ES)" means liquid chromatography followed by mass spectroscopy using electrospray ionization.

"MS (ES)" means mass spectroscopy using electrospray ionization.

"Morpholine, polymer-bound" means morpholine N-linked to a polymer such as polystyrene for use as a catalyst, as for example Aldrich product number 49, 381-3: Morpholine, polymer-bound, 1% cross-linked, 200-400 mesh.

"SCX chromatography" means chromatography on a SCX column or cartridge.

"SCX column" or "SCX cartridge", as used herein, refers to a Varian Bond Elute® silica based strong cation exchange resin column or disposable cartridge or equivalent (as for example a SCX-2 cartridge).

While all of the compounds of the present invention are useful as 5-HT$_7$ antagonists, certain classes are preferred, as for example, compounds having any of the following enumerated selections of substituents:

1) $R^1$ is selected from the group consisting of phenyl optionally substituted with methoxy or 1 to 3 independently selected fluoro or chloro substituents; pyrazol-4-yl optionally substituted with 1 or 2 independently selected methyl or ethyl substituents; and imidazolyl optionally substituted with 1 or 2 methyl groups;
2) $R^1$ is selected from the group consisting of phenyl optionally substituted with methoxy or 1 to 3 fluoro substituents; and pyrazol-4-yl optionally substituted with 1 or 2 methyl or ethyl substituents;
3) $R^1$ is 1-methylpyrazol-4-yl or 1,3-dimethylpyrazol-4-yl;
4) $R^1$ is 1-methylpyrazol-4-yl;
5) $R^1$ is 1,3-dimethylpyrazol-4-yl;
6) $R^1$ is phenyl optionally substituted with methoxy or 1 to 3 independently selected fluoro or chloro substituents;
7) $R^1$ is phenyl;
8) $R^1$ is phenyl substituted in the 4-position with methoxy or fluoro;
9) $R^1$ is 4-fluorophenyl;
10) $R^2$ is methyl;
11) $R^2$ is hydrogen;
12) m is 0;
13) $R^3$ is fluoro, hydroxymethyl, methoxymethyl, or cyanomethyl;
14) $R^3$ is fluoro or methoxymethyl;
15) $R^3$ is methoxymethyl;
16) $R^3$ is fluoro;

Generally, pyrazinyl compounds are preferred over pyridyl compounds (i.e. A is —CH═). Of pyrazinyl compounds, preferred ones are those having selections of substituents according to any one of paragraphs 1 through 16 above. Of pyridyl compounds, preferred ones are those having selections of substituents according to any one of paragraphs 1 through 16 above.

The preferred definitions listed in paragraphs 1) through 16) are the preferred selections for each substituent $R^1$, $R^2$, and $R^3$ individually and independently from each other. As such, for any given selection of a preferred substituent $R^{1-3}$ above, further preferred compounds are those having the first selected preferred substituent and also having a preferred selection for one or more of the other substituents $R^{1-3}$ above. As examples of such preferred combinations, but not to be construed as limiting, the following combinations of preferred selections are preferred combinations:

17) any one preferred selection according to paragraphs 1) through 9) (i.e. preferred selections for $R^1$) in combination with any one preferred selection according to paragraphs 13) through 16) (i.e. preferred selections for $R^3$);
18) compounds wherein $R^1$ is selected from the group consisting of phenyl optionally substituted with methoxy or 1 to 3 independently selected fluoro or chloro substituents; pyrazol-4-yl optionally substituted with 1 to 2 independently selected methyl or ethyl substituents; and imidazolyl optionally substituted with 1 or 2 methyl groups, and $R^3$ is fluoro, hydroxymethyl, methoxymethyl, or cyanomethyl;
19) compounds wherein $R^1$ is selected from the group consisting of phenyl optionally substituted with methoxy or 1 to 3 independently selected fluoro or chloro substituents; pyrazol-4-yl optionally substituted with 1 to 2 independently selected methyl or ethyl substituents; and imidazolyl optionally substituted with 1 or 2 methyl groups, and $R^3$ is fluoro or methoxymethyl;
20) compounds wherein $R^1$ is selected from the group consisting of phenyl optionally substituted with methoxy or 1 to 3 fluoro substituents; and pyrazol-4-yl optionally substituted with 1 to 2 methyl or ethyl substituents, and $R^3$ is fluoro, hydroxymethyl, methoxymethyl, or cyanomethyl;
21) compounds wherein $R^1$ is selected from the group consisting of phenyl optionally substituted with methoxy or 1 to 3 fluoro substituents; and pyrazol-4-yl optionally substituted with 1 to 2 methyl or ethyl substituents, and $R^3$ is fluoro or methoxymethyl;
22) compounds wherein $R^1$ is 1-methylpyrazol-4-yl or 1,3-dimethylpyrazol-4-yl, and $R^3$ is fluoro, hydroxymethyl, methoxymethyl, or cyanomethyl;
23) compounds wherein $R^1$ is 1-methylpyrazol-4-yl or 1,3-dimethylpyrazol-4-yl, and $R^3$ is fluoro or methoxymethyl;

Specific preferred compounds of the present invention are those described in the Examples herein, including the free bases and the pharmaceutically acceptable salts thereof. Of the exemplified compounds, one particularly preferred compound is 1-methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide and/or a pharmaceutically acceptable salt thereof.

General Schemes

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. All substituents, unless otherwise indicated, are as previously defined, and all reagents are well known and appreciated in the art.

Scheme I below, shows one suitable synthetic sequence for preparing pyrazine compounds of the present invention. In this scheme, 2,3-dichloropyrazine (1) is nucleophilically substituted with mono-N-protected piperazine to provide piperazinopyrazine (2). Deprotection and a reductive amination reaction between (3) and aldehyde (4) [the synthesis of (4) is outlined in Scheme II] provides the Boc-protected amine (5). Deprotection followed by acylation with suitably substituted aryl or heteroaryl sulfonyl chloride acylating agents provide intermediate (7). Finally a Suzuki reaction using an appropriately substituted or unsubstituted phenyl boronic acid (8) in the presence of a suitable palladium catalysis provides the desired products (9).

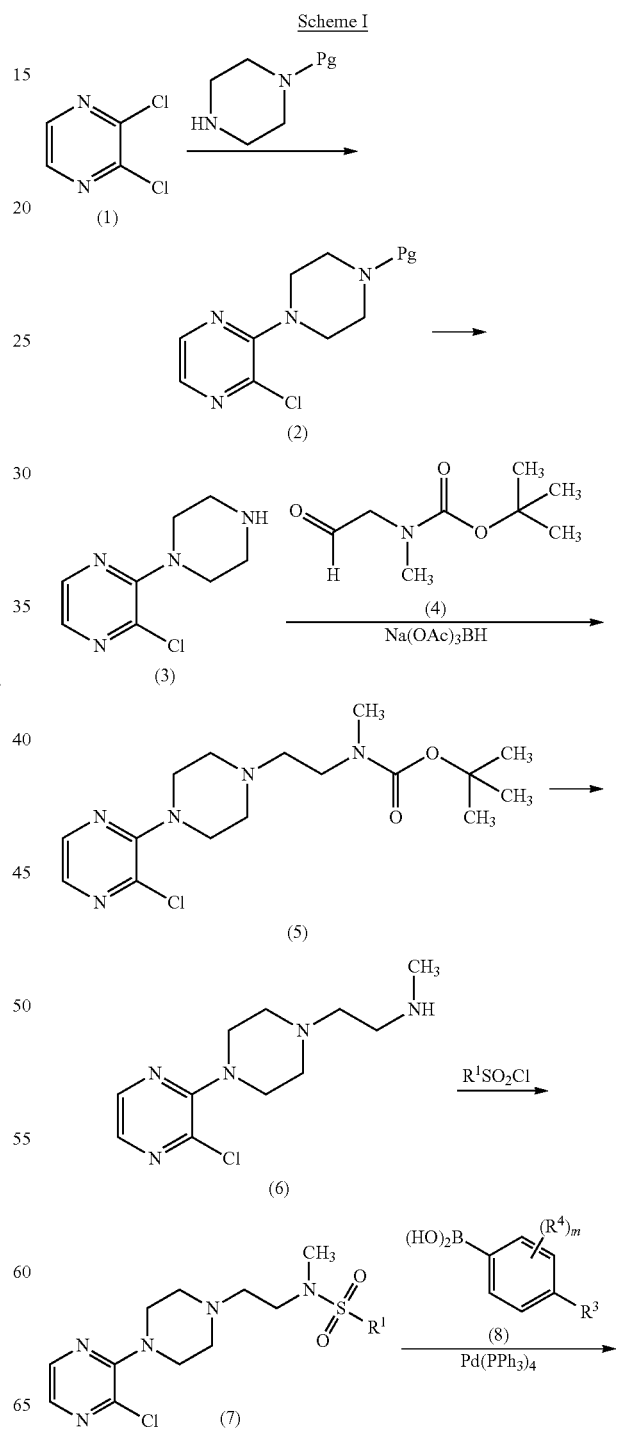

-continued

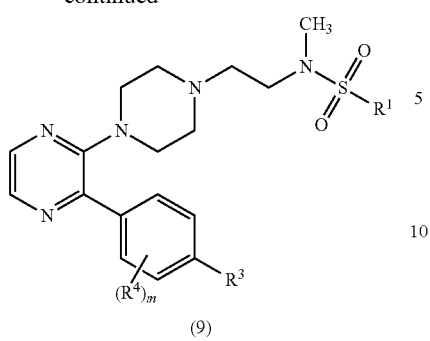

(9)

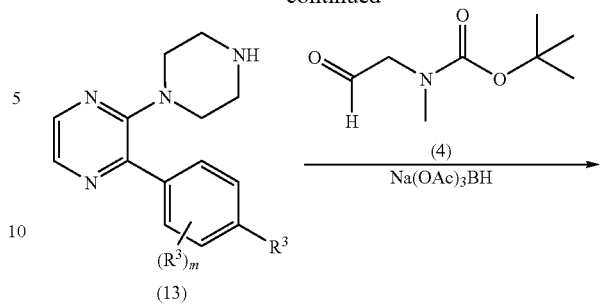

(13)

(14)

(15)

(9)

Although phenyl boronic acid (8) is used in the above illustration (Scheme I) it will be appreciated that other reagents could be used to provide the products (9) (e.g. phenyl stannanes, phenyl zincates, or phenyl Grignards with an appropriate catalyst). Similarly a variety of N-protecting groups may be used, together with appropriate deprotection methods, as is readily appreciated in the art. Exemplary protecting groups include, but are not limited to Boc, acetyl, benzyl, benzyloxycarbonyl or ethoxycarbonyl. The skilled chemist will also appreciate that the above reactions are amenable to a variety of solvents and reaction conditions and that optimal conditions will depend on the particular compound being synthesized.

The order of the coupling steps in Scheme I may be altered if desired, as for example as described in Scheme II. Thus the N-protected piperazine (2) may be coupled first with the boronic acids (etc) to yield (12). This may then be deprotected and subjected to reductive amination with (4), followed finally with the deprotection and acylation to afford the required products (9), as above.

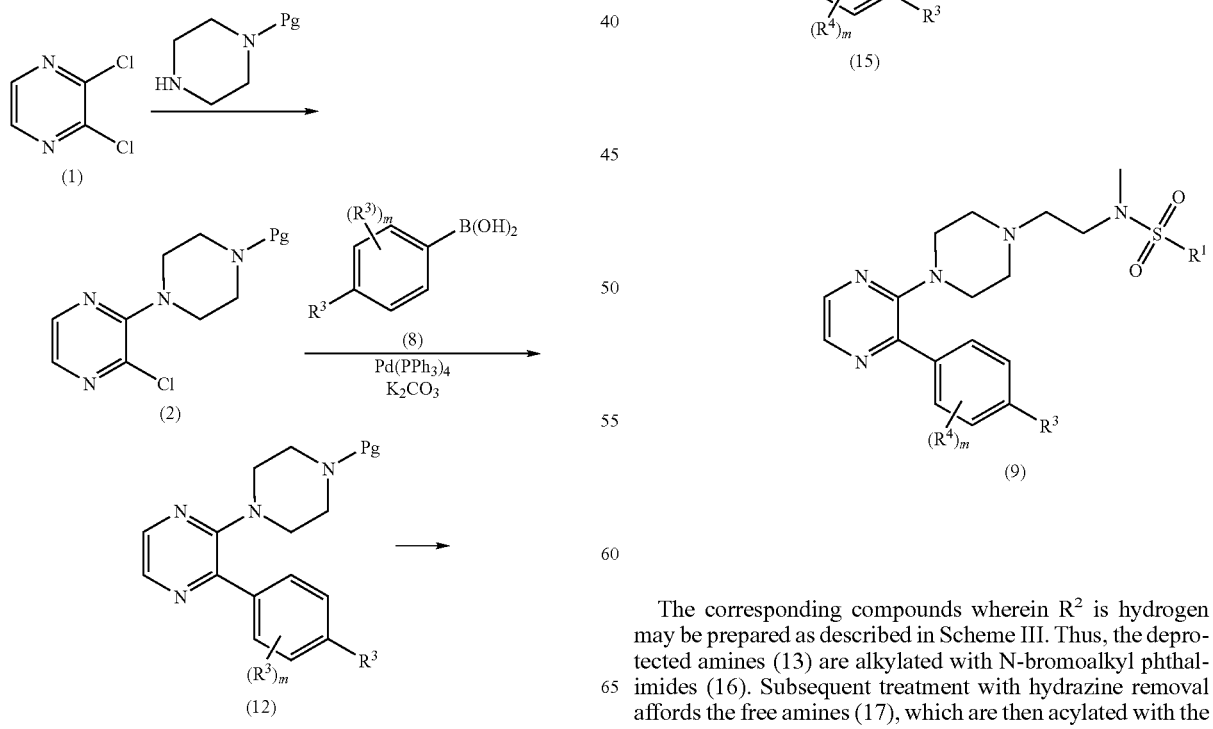

The corresponding compounds wherein $R^2$ is hydrogen may be prepared as described in Scheme III. Thus, the deprotected amines (13) are alkylated with N-bromoalkyl phthalimides (16). Subsequent treatment with hydrazine removal affords the free amines (17), which are then acylated with the desired acylating agents to afford the desired products (18).

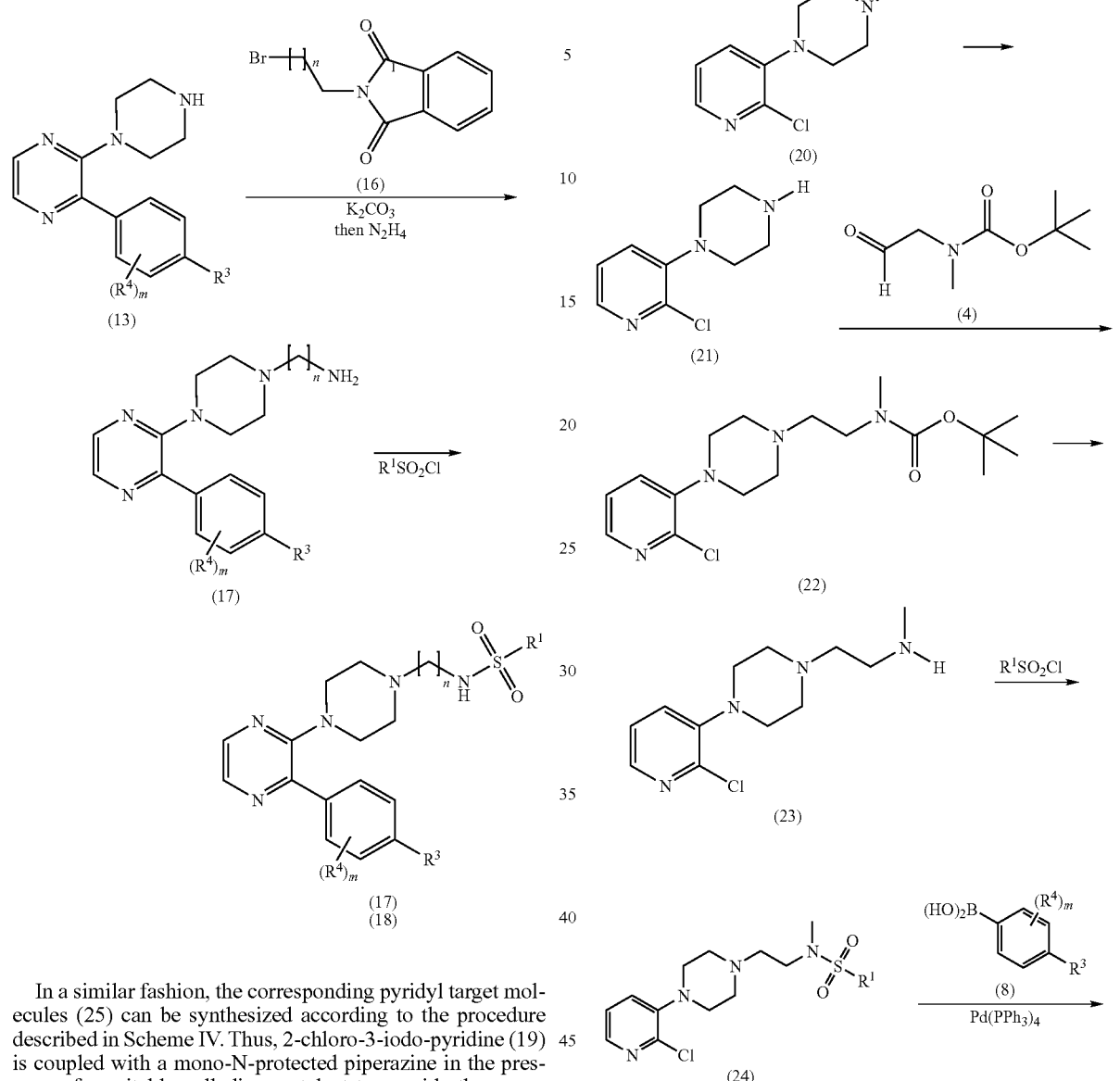

In a similar fashion, the corresponding pyridyl target molecules (25) can be synthesized according to the procedure described in Scheme IV. Thus, 2-chloro-3-iodo-pyridine (19) is coupled with a mono-N-protected piperazine in the presence of a suitable palladium catalyst to provide the corresponding N-protected 2-chloro-3-piperazinopyridine (20). This is followed by deprotection to (21) and reductive amination reaction with aldehyde (4) to afford the protected amine (22). Deprotection to amine (23) and acylation with the appropriate sulfonylchloride provides sulphonamides (24). Finally, Suzuki coupling with the appropriately substituted phenyl boronic acid (8) yields the desired pyridyl products (25).

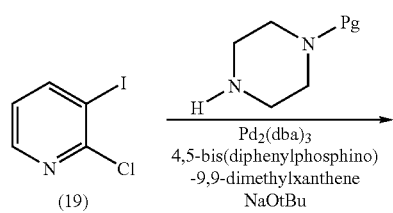

Although a phenyl boronic acid (8) is used in the above illustration, it will be appreciated that other phenylating reagents may also be used (e.g. phenyl stannanes, phenyl zincates, or phenyl Grignards with appropriate catalysis).

Further, compounds wherein $R^3$ is may be prepared according to Scheme V.

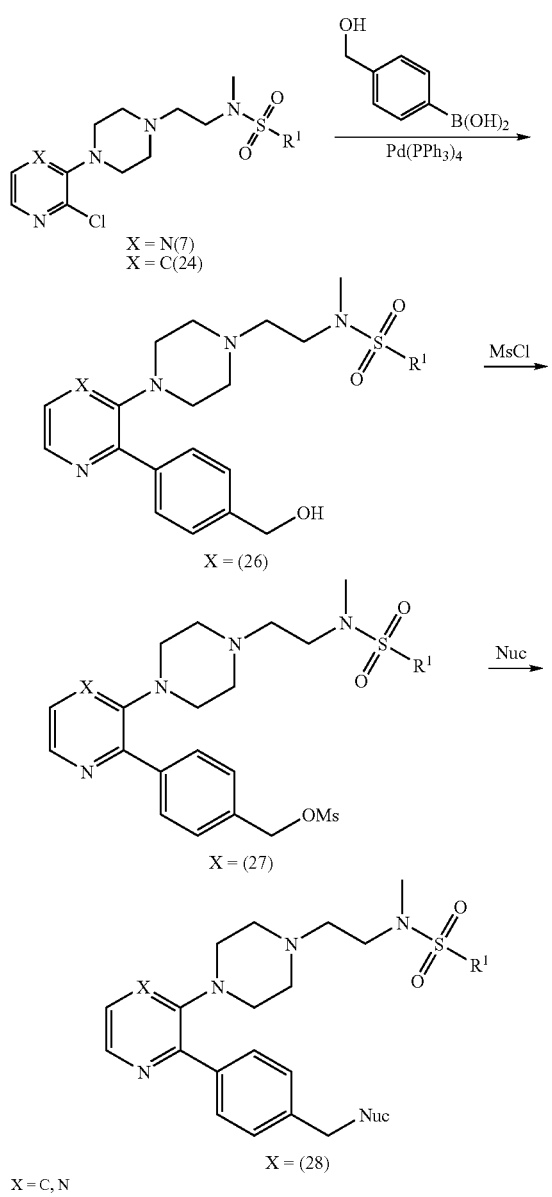

Scheme V

X = N(7)
X = C(24)

X = (26)

X = (27)

X = (28)
X = C, N

Thus the product of Suzuki reaction between (7) or (24) with 4-hydroxymethyl-boronic acid yields the products (26: X=N or C, respectively). Subsequent mesylation and SN2 displacement with suitable nucleophiles yields the target molecules (28: X=N or C, respectively).

The following Preparations and Examples are illustrative of methods useful for the synthesis of the compounds of the present invention. The names for many of the compounds illustrated in the preparations and examples are provided from structures drawn with ChemDraw®, version 7.0 software or Autonom 2000 for ISIS/Draw.

Preparation 1: 3'-Chloro-2,3,5,6-tetrahydro-[1,2'] bipyrazinyl-4-carboxylic acid t-butyl ester Charge a 2 L 3-neck round bottom flask with 2,3-dichloropyrazine (78.7 g, 0.532 mol), piperazine-1-carboxylic acid t-butyl ester (100 g, 0.537 mol), potassium carbonate (88.2 g, 0.638 mol) followed by N,N-dimethylacetamide (0.780 L), and heat the resultant slurry to 110° C. under nitrogen with vigorous stirring. Cool to room temperature, add water (0.390 L) and t-butyl methyl ether (0.390 L), and stir the mixture for 60 min. Stop stirring and separate the layers. Wash the organic layer with water (2×200 mL), dry over $MgSO_4$, filter and concentrate to give the title preparation as a yellow syrup (145 g, 91% yield).

Preparation 2: 3'-chloro-3,4,5,6-tetrahydro-2H-[1,2'] bipyrazine

To a solution of 3'-chloro-2,3,5,6-tetrahydro-[1,2']bipyrazinyl-4-carboxylic acid t-butyl ester (10 g, 33.4 mmol, 1 eq) in 1,4-dioxane (160 mL) add a 4 M solution of hydrochloric acid in 1,4-dioxane (80 mL, 0.3 mol, 10 eq) and stir under nitrogen at room temperature overnight. Dilute with DCM (600 mL) then basify with 50% aqueous sodium hydroxide. Add water (100 mL), separate the layers and extract the aqueous twice with DCM (200 mL). Combine the organic extracts, wash with saturated aqueous sodium chloride, dry (magnesium sulfate), filter, and concentrate to give 3'-chloro-3,4,5,6-tetrahydro-2H-[1,2']bipyrazinyl as a viscous oil which solidifies on standing (6.39 g, 96%). MS (ES): m/z=199.1, 201.1 $[M+H]^+$.

Preparation 3: 3'-(4-Fluoro-phenyl)-3,4,5,6-tetrahydro-2H-[1,2']bipyrazine dihydrochloride Charge a reactor with 2,3-dichloropyrazine (73.6 g, 0.497 mol, 1.0 equiv), piperazine-1-carboxylic acid t-butyl ester (101.9 g, 0.547 mol, 1.1 equiv) and powdered potassium carbonate (164.8 g, 1.19 mol, 2.4 equiv). Add N,N-dimethylacetamide (1.1 L) and heat to 110° C. under nitrogen for 5 hr. Cool the reaction to room temperature, and add 4-fluorophenylboronic acid (83.4 g, 0.596 mol, 1.2 equiv), tetrakis(triphenyl-phosphine)palladium(0) (2.87 g, 2.5 mmol, 0.005 equiv) and water (442 mL). Heat the reaction to 110° C. under a nitrogen atmosphere for 5 hr. Cool the reaction to 60° C. and dilute with water (800 mL) and methyl t-butyl ether (1.0 L). Cool to room temperature and separate the resulting layers. Wash the organic layer with 200 mL of water, separate the layers, and concentrate to give 3-(4-fluorophenyl)-2-[4-(t-butyloxycarbonyl)piperazin-1-yl]pyrazine as a light yellow solid that is taken into the next step without further purification.

Charge the crude 3-(4-fluorophenyl)-2-[4-(t-butyloxycarbonyl)piperazin-1-yl]pyrazine to a reactor along with n-butanol (1.67 L) and toluene (99 mL). Heat the reaction mixture to 60° C., and add a solution of HCl in n-butanol (835 mL, prepared by adding 2.33 moles of acetyl chloride to 668 mL of n-butanol at 0° C.) in situ to the reaction dropwise. After the addition is complete, stir at 60° C. for 2 hr. and cool to room temperature. Stir the resulting solids at room temperature, filter, wash with n-butanol (200 mL), and dry overnight in a vacuum oven at 70° C. to give the title intermediate as a yellow solid (148.95 g, 86% yield over four steps, correcting for n-butanol trapped in the solids). MS (ES): m/z=259 $[M+H]^+$.

Preparation 4: 3'-(2-Fluoro-phenyl)-3,4,5,6-tetrahydro-2H-[1,2']bipyrazine dihydrochloride Prepare the title intermediate using essentially the same methods as for Preparation 3, using 2-fluorophenylboronic acid. MS (ES) m/z=259 [M+H]

Preparation 5: 3'-(4-Methoxymethyl-phenyl)-2,3,5,6-tetrahydro-[1,2']bipyrazinyl-4-carboxylic acid tert-butyl ester Dissolve 3'-chloro-2,3,5,6-tetrahydro-[1,2']bipyrazinyl-4-carboxylic acid tert-butyl ester (3.0 g, 10.1 mmol, 1 eq.) in 1,2 dimethoxyethane (6 mL). Add 4-methoxymethyl-benzene boronic acid (2.01 g, 12.12 mmol, 1.2 eq.). Add tetrakis (triphenylphosphine)-palladium (1.17 g, 1.01 mmol, 0.1 eq.) followed by potassium carbonate (3.77 g, 27.3 mmol, 2.7 eq.). Heat the reaction mixture at 100° C. for 17 hr. Partition the reaction mixture between EtOAc and water. Separate layers. Extract the aqueous layer with dichloromethane. Combine organic layers, dry over anhydrous $Na_2SO_4$, filter and concentrate. Purify by normal phase chromatography with 10-30% EtOAc/hexane to afford the title preparation (3.7 g, 96% yield). LC MS (ES): m/z=385.3 [M+H].

Preparation 6: 3'-(4-Methoxymethyl-phenyl)-3,4,5,6-tetrahydro-2H-[1,2']bipyrazinyl Dissolve 3'-(4-methoxymethyl-phenyl)-2,3,5,6-tetrahydro-[1,2']bipyrazinyl-4-carboxylic acid tert-butyl ester (3.72 g, 9.70 mmol) in dichloromethane (25 mL). Add cold trifluoroacetic acid (30 mL, 44.2 g, 388 mmol, 40 eq.). Stir for 1 hr. Partition the crude reaction mixture between aq. 5N NaOH and dichloromethane. Separate the layers (pH aqueous layer=14). Extract the aqueous layer with dichloromethane (2×50 mL). Combine organic layers, dry over anhydrous $Na_2SO_4$, filter and concentrate to obtain the title preparation (2.76 g, 100% yield). LC MS (ES): m/z=285.0 [M+H].

Preparation 7: Methyl-(2-oxo-ethyl)-carbamic acid t-butyl ester

Add 2-methylaminoethanol (1.00 eq.; 1.24 moles; 93.44 g) to chloroform (6.23 moles; 744 g) under a nitrogen atmosphere and cool to about 5° C. Add dropwise, a solution of di-t-butyldicarbonate (1.24 moles; 280 mL) in chloroform (200 mL), keeping the reaction mixture cooled below about 5° C. Stir the reaction mixture at room temperature overnight. Concentrate to provide (2-hydroxy-ethyl)-methyl-carbamic acid t-butyl ester as a clear oil (230 g).
Combine under a nitrogen atmosphere, dichloromethane (37.91 moles; 2.43 L), dimethyl sulfoxide (7.30 moles; 518.4 mL), triethylamine (1.85 moles; 257.7 mL), and (2-hydroxy-ethyl)-methyl-carbamic acid t-butyl ester (924.5 mmoles; 162.0 g). Add in steps sulfur trioxide:pyridine complex (1.849 moles; 300.3 g), maintaining the reaction temperature less than 20° C. Stir the reaction mixture at ambient temperature overnight. Add 1.0 L water, separate the organic layer, wash with 10% citric acid in water (800 mL), water and brine. Concentrate and pass through a silica plug, eluting with 20% ethyl acetate/hexanes. Add toluene (200 mL) and concentrate to provide the title intermediate (yield 62.45%, 100 g).

Preparation 8: {2-[3'-(4-Methoxymethyl-phenyl)-2,3,5,6-tetrahydro-[1,2']bipyrazinyl-4-yl]-ethyl}-methyl-carbamic acid tert-butyl ester Dissolve 3'-(4-methoxymethyl-phenyl)-3,4,5,6-tetrahydro-2H-[1,2']bipyrazinyl (1.76 g, 6.2 mmol, 1 eq.) in 1,2 dichloroethane (20 mL). Add methyl-(2-oxo-ethyl)-carbamic acid tert-butyl ester (1.13 g, 6.51 mmol, 1.05 eq.). Add sodium triacetoxyborohydride (1.97 g, 9.3 mmol, 1.5 eq.). Stir at room temperature for 18 hr. Partition the reaction mixture between aqueous saturated $NaHCO_3$ and dichloromethane. Separate the layers. Extract the organic layer with dichloromethane (2×100 mL). Combine the organic layers, dry over anhydrous $Na_2SO_4$, filter and concentrate. Purify by normal phase chromatography with 30% EtOAc/hexane—100% EtOAc to afford the title preparation (1.01 g, 37% yield). MS (loop): m/z=442.3 [M+H].

Preparation 9: {2-[3'-(4-Methoxymethyl-phenyl)-2,3,5,6-tetrahydro-[1,2']bipyrazinyl-4-yl]-ethyl}-methylamine Dissolve {2-[3'-(4-methoxymethyl-phenyl)-2,3,5,6-tetrahydro-[1,2']bipyrazinyl-4-yl]-ethyl}-methyl-carbamic acid tert-butyl ester (1.01 g, 2.3 mmol, 1 eq.) in dichloromethane (20 mL). Add trifluoroacetic acid (10.5 g, 7.1 mL, 92 mmol, 40 eq.). Stir at room temperature for 1.5 hr. Partition the reaction mixture between aqueous 5N NaOH (pH aqueous layer=14) and dichlormethane. Separate the layers. Extract the aqueous layer with dichloromethane (2×50 mL). Combine the organic layers, dry over anhydrous $Na_2SO_4$, filter and concentrate to afford the title preparation (0.76 g, 97% yield). MS (loop): m/z=342.3 [M+H].

Preparation 10: {2-[3'-(4-Fluoro-phenyl)-2,3,5,6-tetrahydro-[1,2']bipyrazinyl-4-yl]-ethyl}-methyl-carbamic acid tert-butyl ester Dissolve 3'-(4-fluoro-phenyl)-3,4,5,6-tetrahydro-2H-[1,2']bipyrazinyl (2.5 g, 9.7 mmol, 1 eq.) in 1,2 dichloroethane (20 mL). Add methyl-(2-oxo-ethyl)-carbamic acid tert-butyl ester (1.77 g, 10.19 mmol, 1.05 eq.). Add sodium triacetoxyborohydride (3.10 g, 14.6 mmol, 1.5 eq.). Stir at room temperature for 18 hr. Partition the reaction mixture between aqueous saturated $NaHCO_3$ and dichloromethane. Separate the layers. Extract the organic layer with dichloromethane (2×100 mL). Combine the organic layers, dry over anhydrous $Na_2SO_4$, filter and concentrate. Purify by normal phase chromatography with 30% EtOAc/hexane—100% EtOAc to afford the title preparation (3.8 g, 97% yield). MS (loop): m/z=416.3 [M+H].

Preparation 11: {2-[3'-(4-Fluoro-phenyl)-2,3,5,6-tetrahydro-[1,2']bipyrazinyl-4-yl]-ethyl}-methylamine Dissolve {2-[3'-(4-fluoro-phenyl)-2,3,5,6-tetrahydro-[1,2']bipyrazinyl-4-yl]-ethyl}-methyl-carbamic acid tert-butyl ester (3.8 g, 9.16 mmol, 1 eq.) in dichloromethane (20 mL). Add trifluoroacetic acid (41.2 g, 27.8 mL, 366.4 mmol, 40 eq.). Stir at room temperature for 1.5 hr. Partition the reaction mixture between aqueous 5N NaOH (pH aqueous layer=14) and dichlormethane. Separate the layers. Extract the aqueous layer with dichloromethane (2×50 mL). Combine the organic layers, dry over anhydrous $Na_2SO_4$, filter and concentrate to afford the title preparation (3.04 g, 100% yield). MS (loop): m/z=316.3 [M+H].

Preparation 12: {2-[3'-(2-Fluoro-phenyl)-2,3,5,6-tetrahydro-[1,2']bipyrazinyl-4-yl]-ethyl}-methylamine Prepare the title intermediate using essentially the same methods as Preparations 10 and 11, using 3'-(2-fluoro-phenyl)-3,4,5,6-tetrahydro-2H-[1,2']bipyrazine dihydrochloride.

Preparation 13: 2-[3'-(4-Fluorophenyl)-2,3,5,6-tetrahydro-[1,2']bipyrazinyl-4-yl]-ethylamine Dissolve 3'-(4-fluorophenyl)-3,4,5,6-tetrahydro-2H-[1,2']bipyrazinyl (1.00 g, 3.87 mmol), N-(3-bromoethyl)phthalimide (3.87 mmol), and potassium carbonate (0.536 g, 3.87 mmol) in acetone (33 mL). Reflux the reaction for 18 hr. Cool to room temperature and concentrate. Dissolve in dichloromethane and wash with water, followed by saturated aqueous NaCl. Extract combined aqueous layers with dichloromethane, dry (magnesium sulfate), filter, concentrate and purify (silica gel chromatography, eluting with 0:100 to 10:90 methanol:dichloromethane), to give 2-{3-[3'-(4-fluorophenyl)-2,3,5,6-tetrahydro-[1,2']bipyrazinyl-4-yl]-ethyl}-isoindole-1,3-dione.
Dissolve 2-{3-[3'-(4-fluorophenyl)-2,3,5,6-tetrahydro-[1,2']bipyrazinyl-4-yl]-ethyl}-isoindole-1,3-dione in ethanol (80 mL). Add hydrazine hydrate (0.793 g, 15.8 mmol) and reflux for 18 hr. Cool to room temperature and filter, washing with ethanol. Concentrate, add 1 N NaOH (100 mL), and stir at room temperature for five min. Extract aqueous solution three times with diethyl ether and wash combined organic layers once with saturated aqueous NaCl, dry (magnesium sulfate), filter, concentrate and purify (SCX chromatography) to give the title preparation (503 mg, 90% yield). MS (ES): m/z=302 [M+H]$^+$.

Preparation 14: N-{2-[3'-(4-Fluoro-phenyl)-2,3,5,6-tetrahydro-[1,2']bipyrazinyl-4-yl]-2-oxo-ethyl}-N-methyl-benzenesulfonamide Dissolve (benzenesulfonyl-methyl-amino)-acetic acid (0.150 g, 0.654 mmol) in dichloromethane (5 mL). Add 1-hydroxybenzotriazole hydrate (0.081 g, 0.595 mmol) followed by 1-[3-(dimethylamino)propyl]-3-ethylcarbodiimide hydrochloride (0.114 g, 0.595 mmol). Add 3'-(4-fluoro-phenyl)-3,4,5,6-tetrahydro-2H-[1,2']bipyrazinyl (0.154 g, 0.595 mmol) and stir at ambient temperature for 18 hr. Add dichloromethane and water and separate layers. Extract the aqueous layer three times with dichloromethane. Dry the combined organic layers over magnesium sulfate, filter and concentrate under reduced pressure to give residue. Purify the residue by chromatography on silica gel eluting with 50-100% ethylacetate/hexanes to give the title preparation (193 mg, 69% yield). MS (ES+) m/z: 470 (M+H)$^+$.

Preparation 15: [2-(3'-Chloro-2,3,5,6-tetrahydro-[1,2']bipyrazinyl-4-yl)-ethyl]-methyl-amine dihydrochloride Add methyl-(2-oxo-ethyl)-carbamic acid t-butyl ester (27.69 mmoles; 4.80 g) and 3'-chloro-3,4,5,6-tetrahydro-2H-[1,2']bipyrazine (25.17 mmoles; 5.00 g) to 1,2 dichloroethane (50.0 mL) on ice. Add sodium triacetoxyborohydride (32.7 mmoles; 6.93 g) in 3 portions. Stir the reaction mixture at room temperature overnight. Quench the reaction with water, separate the organic layer and concentrate. Wash in hexanes and filter to provide [2-(3'-chloro-2,3,5,6-tetrahydro-[1,2']bipyrazinyl-4-yl)-ethyl]-methyl-carbamic acid t-butyl ester as a clear oil.

Cool a solution of methanol to 5° C. Add acetyl chloride (5 equiv.) dropwise and stir the reaction for 10 min. Dissolve the above [2-(3'-chloro-2,3,5,6-tetrahydro-[1,2']bipyrazinyl-4-yl)-ethyl]-methyl-carbamic acid t-butyl ester in toluene and add in one portion to the methanol solution. Stir the homogenous solution at room temperature for 2 hr. Filter the resultant solid and dry in a vacuum oven to provide the title intermediate as the dihydrochloride salt. Recrystallize from ethanol/methanol (10:1).

Preparation 16: N-[2-(3'-Chloro-2,3,5,6-tetrahydro-[1,2']bipyrazinyl-4-yl)-ethyl]-N-methyl-benzenesulfonamide Dissolve [2-(3'-chloro-2,3,5,6-tetrahydro-[1,2']bipyrazinyl-4-yl)-ethyl]-methyl-amine dihydrochloride salt (2.0 g, 6.09 mmol) in dichloromethane (50 mL). Add triethylamine (3.39 mL, 24.4 mmol), and benzenesulfonylchloride (854 µL, 6.69 mmol). Stir at ambient temperature for 18 hr. Add dichloromethane and aqueous 1 N HCl solution. Separate the organic layer and extract the aqueous layer twice with dichloromethane. Combine the organic layers and dry (magnesium sulfate), filter, and concentrate. Purify via SCX chromatography, followed by silica gel chromatography (100:0 to 0:100 hexanes:ethyl acetate) to give the title preparation (1.88 g, 78%). MS (ES): m/z=396 [M+H]$^+$.

Preparation 17: 1-Methyl-1H-pyrazole-4-sulfonic acid [2-(3'-chloro-2,3,5,6-tetrahydro-[1,2']bipyrazinyl-4-yl)-ethyl]-methyl-amide Add triethylamine (0.852 mL, 6.116 mmol) to a stirring solution of [2-(3'-chloro-2,3,5,6-tetrahydro-[1,2']bipyrazinyl-4-yl)-ethyl]-methyl-amine (0.500 g, 1.529 mmol) in dichloromethane (10 mL). Add 1-methyl-1H-pyrazole-4-sulfonyl chloride (0.331 g, 1.834 mmol) at room temperature. Stir at room temperature for 18 hr. Dilute with dichloromethane and saturated aqueous sodium bicarbonate. Separate and extract the aqueous layer with dichloromethane. Combine the organic layers, dry over sodium sulfate, filter, and concentrate. Purify the resulting material by silica gel chromatography eluting with hexanes:acetone 6:4 to 4:6 to afford the title preparation (0.514 g, 84% yield). MS ES: m/z=400 [M+H]$^+$.

Preparation 18: Methanesulfonic acid 4-(4-{2-[methyl-(1-methyl-1H-pyrazole-4-sulfonyl)-amino]-ethyl}-3,4,5,6-tetrahydro-2H-[1,2']bipyrazinyl-3'-yl)-benzyl ester Add triethylamine (0.653 mmol, 0.091 mL) to a stirred solution of 1-methyl-1H-pyrazole-4-sulfonic acid {2-[3'-(4-hydroxymethyl-phenyl)-2,3,5,6-tetrahydro-[1,2']bipyrazinyl-4-yl]-ethyl}-methyl-amide (0.594 mmol, 0.280 g) in dry dichloromethane (5 mL) at room temperature under nitrogen. Add methanesulfonyl chloride (0.653 mmol, 0.051 mL). Allow the mixture to warm to room temperature and stir 1 hr. Dilute with dichloromethane and brine. Separate and extract the aqueous phase with dichloromethane. Combine organics, dry over Na$_2$SO$_4$, and concentrate to dryness to afford the title preparation (0.330 g, crude). The material is used without further purification. MS ES: m/z=550 [M+H]$^+$.

Preparation 19: 1,3-Dimethyl-1H-pyrazole-4-sulfonic acid [2-(3'-chloro-2,3,5,6-tetrahydro-[1,2']bipyrazinyl-4-yl)-ethyl]-methyl-amide Dissolve [2-(3'-chloro-2,3,5,6-tetrahydro-[1,2']bipyrazinyl-4-yl)-ethyl]-methyl-amine hydrochloride salt (0.5 g, 1.29 mmol) in dichloromethane (10 ml) and cool in an ice-bath. Add triethylamine (0.90 ml, 6.44 mmol) and then 1,3-dimethylpyrazole-4-sulfonyl chloride (250 mg, 1.29 mmol). Remove the ice-bath and allow to warm to ambient temperature and allow to stir for 2 hr. Wash the organic phase with aqueous sodium bicarbonate, brine and water. Dry over sodium sulfate and concentrate. Purify by chromatography, eluting with 1:2 hexanes:acetone to afford the title preparation (535 mg, 100% yield) as a white foam. MS ES: m/z=414 [M+H]$^+$.

Preparation 20: 1-Methyl-1H-pyrazole-4-sulfonic acid [2-(3'-chloro-2,3,5,6-tetrahydro-[1,2']bipyrazinyl-4-yl)-ethyl]-methyl-amide Dissolve [2-(3'-chloro-2,3,5,6-tetrahydro-[1,2']bipyrazinyl-4-yl)-ethyl]-methyl-amine hydrochloride salt (1.0 g, 2.57 mmol) in dichloromethane (20 ml) and cool in an ice-bath. Add triethylamine (1.79 ml, 12.87 mmol) and then 1-methylpyrazole-4-sulfonyl chloride (465 mg, 2.57 mmol). Remove the ice-bath and allow to warm to ambient temperature and allow to stir for 20 hr. Wash the combined organic layers with aqueous sodium bicarbonate, brine and water. Dry over sodium sulfate and concentrate. Purify by chromatography, eluting with 1:2 hexanes:acetone to afford the title compound (1.1 g, 97% yield) as a white foam. MS ES: m/z=400 [M+H]$^+$.

Preparation 21: Pyridine-3-sulfonic acid [2-(3'-chloro-2,3,5,6-tetrahydro-[1,2']bipyrazinyl-4-yl)-ethyl]-methyl-amide Add triethylamine (0.426 mL, 3.058 mmol) to a stirring solution of [2-(3'-chloro-2,3,5,6-tetrahydro-[1,2']bipyrazinyl-4-yl)-ethyl]-methyl-amine (0.200 g, 0.612 mmol) in dichloromethane (5 mL). Add pyridine-3-sulfonyl chloride hydrochloride salt (0.157 g, 0.734 mmol) at room temperature. Stir at room temperature for 20 min. Dilute with dichloromethane and saturated aqueous sodium bicarbonate. Separate and extract the aqueous fraction with dichloromethane. Combine the organic fractions, dry over sodium sulfate, filter, and concentrate. Purify the resulting material by silica gel chromatography eluting with hexanes:acetone 4:1 to afford the title preparation (0.220 g, 91% yield). MS ES: m/z=397 [M+H]$^+$.

Preparation 22: Pyridine-2-sulfonic acid [2-(3'-chloro-2,3,5,6-tetrahydro-[1,2']bipyrazinyl-4-yl)-ethyl]-methyl-amide Prepare the title preparation using essentially the same methods as described in preparation 21, using pyridine-2-sulfonyl chloride (69% yield).

Preparation 23: 4-(2-Chloro-pyridin-3-yl)-piperazine-1-carboxylic acid t-butyl ester Dissolve 2-chloro-3-iodopyridine (2.0 g, 8.37 mmol) in toluene (7 mL). Add piperazine-1-carboxylic acid t-butyl ester (1.2 g, 6.4 mmol), followed by the addition of tris(dibenzylideneacetone)dipalladium(0) (0.12 g, 0.13 mmol), 4,5-bis(diphenyl-phosphino)-9,9-dimethylxanthene (0.23 g, 0.39 mmol), and sodium t-butoxide (0.93 g, 9.7 mmol). Heat at 100° C. for 3.5 hr. Concentrate and partition the residue between EtOAc and water. Extract the aqueous phase twice with ethyl acetate. Wash combined organic layers with brine. Dry the organic extracts (sodium sulfate), filter, concentrate and purify (silica gel chromatography, eluting with 0:100 to 20:80 ethyl acetate:hexanes), to give the title preparation (95%). MS (ES): m/z=298 [M+H]$^+$.

Preparation 24: 1-(2-Chloro-pyridin-3-yl)-piperazine hydrochloride salt

Dissolve 4-(2-chloro-pyridin-3-yl)-piperazine-1-carboxylic acid tert-butyl ester (8.300 g, 27.872 mmol) in dichloromethane (200 mL). Slowly add 4N HCl in dioxane (42 mL). Stir at room temperature for 8 hours. Concentrate and wash the resulting solid with diethyl ether to afford the title preparation (7.500 g, 99% yield). MS ES: m/z=198 [M+H]$^+$.

Preparation 25: {2-[4-(2-Chloro-pyridin-3-yl)-piperazin-1-yl]-ethyl}-methyl-carbamic acid tert-butyl ester Convert 1-(2-chloro-pyridin-3-yl)-piperazine hydrochloride salt (5.800 g) to the free base by passing through SCX resin (15 g column) eluting with dichloromethane, methanol, and then 2N ammonia in methanol. Concentrate the appropriate fractions to afford the free base (4.3 g). Dissolve the free base (21.754 mmol, 4.300 g) in dry 1,2-dichloroethane (100 mL) and add methyl-(2-oxo-ethyl)-carbamic acid tert-butyl ester (5.652 g, 32.631 mmol) at room temperature under nitrogen. Cool to 0° C. and stir for 5 min. Slowly add sodium triacetoxyborohydride (43.508 mmol, 9.221 g) at 0° C., allow the reaction mixture to gradually warm to room temperature and stir 18 hr. Concentrate and dilute with ethyl acetate. Add brine slowly. Separate the phases and extract the aqueous phase with ethyl acetate. Combine the organic phases, dry over sodium sulfate, filter, and concentrate. Purify the resulting material by silica gel chromatography eluting with hexanes:acetone 1:1 to afford the title preparation (4.960 g, 64% yield). MS ES: m/z=355 [M+H]$^+$.

Preparation 26: {2-[4-(2-Chloro-pyridin-3-yl)-piperazin-1-yl]-ethyl}-methyl-amine hydrochloride salt Dissolve {2-[4-(2-chloro-pyridin-3-yl)-piperazin-1-yl]-ethyl}-methyl-carbamic acid tert-butyl ester (4.900 g, 13.807 mmol) in dichloromethane (100 mL). Slowly add 4N HCl in dioxane (20.711 mL, 82.845 mmol). Stir at room temperature for 18 hr. Concentrate and wash the resulting solid with diethyl ether to afford the title preparation (7.500 g, 99% yield). MS ES: m/z=255 [M+H]$^+$.

Preparation 27: N-{2-[4-(2-Chloro-pyridin-3-yl)-piperazin-1-yl]-ethyl}-4-fluoro-N-methyl-benzene-sulfonamide Add triethylamine (0.850 mL, 6.103 mmol) to a stirring solution of {2-[4-(2-chloro-pyridin-3-yl)-piperazin-1-yl]-ethyl}-methyl-amine hydrochloride salt (2.000 g, 6.103 mmol) in dichloromethane (10 mL). Stir at room temperature for 5 min. Add 4-fluoro-benzenesulfonyl chloride (0.356 g, 1.831 mmol) at room temperature. Stir at room temperature for 18 hr. Dilute with dichloromethane and saturated aqueous sodium bicarbonate. Separate the phases and extract the aqueous phase with dichloromethane. Combine the organic phases, dry over sodium sulfate, filter, and concentrate. Purify the resulting material by silica gel chromatography eluting with hexanes:acetone 1:1 to afford the title preparation (0.525 g, 83% yield). MS ES: m/z=413 [M+H]$^+$.

Preparation 28: 1-Methyl-1H-pyrazole-4-sulfonic acid {2-[4-(2-chloro-pyridin-3-yl)-piperazin-1-yl]-ethyl}-methyl-amide Add triethylamine (3.403 mL, 24.414 mmol) to a stirring solution of {2-[4-(2-chloro-pyridin-3-yl)-piperazin-1-yl]-ethyl}-methyl-amine hydrochloride salt (2.000 g, 6.103 mmol) in dichloromethane (100 mL). Add 1-methyl-1H-pyrazole-4-sulfonyl chloride (1.102 g, 6.103 mmol) at room temperature. Stir at room temperature for 30 min. Dilute with dichloromethane and saturated aqueous sodium bicarbonate. Separate phases and extract the aqueous phase with dichloromethane. Combine the organic phases, dry over sodium sulfate, filter, and concentrate. Purify the resulting material by silica gel chromatography eluting with hexanes:acetone 1:1 to afford the title preparation (1.600 g, 66% yield). MS ES: m/z=399 [M+H]$^+$.

Preparation 29: 1-Methyl-1H-pyrazole-4-sulfonyl chloride

Add 1-methyl-1H-pyrazole (100 g, 1.18 mol) dropwise to chlorosulfonic acid (325 mL, 4.84 mol) stirring at 0° C. under nitrogen atmosphere. Heat reaction mixture at 110° C. for 3 hr. Cool to room temperature, then pour carefully into crushed ice with stirring. Recover the resulting white solid by vacuum filtration, wash with water, and dry under vacuum. Use the resulting material (72.2 g, 33%) without further purification.

Preparation 30: 1-Methyl-1H-pyrazole-4-sulfonic acid (2,2-dimethoxy-ethyl)-methyl-amide Cool a solution of methylaminoacetaldehyde dimethyl acetal (22.5 mL, 0.18 mol) and triethylamine (26.5 mL, 0.19 mol) to 0° C. in $CH_2Cl_2$, then add dropwise a solution of 1-methyl-1H-pyrazole-4-sulfonyl chloride (30 g, 0.17 mol). Stir the reaction mixture at room temperature overnight, dilute with $CH_2Cl_2$ (500 mL), and wash with water. Dry the combined organics over $Na_2SO_4$, filter and concentrate. The resulting oil is placed under high vacuum and within two hours a resulting off white solid is formed, which is used without further purification (38.22 g, 87%).

Preparation 31: 1-Methyl-1H-pyrazole-4-sulfonic acid methyl-(2-oxo-ethyl)-amide

Treat a solution of 1-methyl-1H-pyrazole-4-sulfonic acid (2,2-dimethoxy-ethyl)-methyl-amide (12.16 g, 46.18 mmol) in $CH_2Cl_2$ with 1.0 M HCl (50 mL). Stir the resulting mixture at reflux for 1 hr., then treat with 5.0 M HCl (50 mL) and further reflux for 2 hr. Cool the reaction to room temperature, extract with EtOAc and $CH_2Cl_2$. Combine the organics, dry over $Na_2SO_4$, filter and concentrate to provide the title intermediate as an oil (8.96 g, 89.3%).

Alternatively, 1-methyl-1H-pyrazole-4-sulfonic acid (2,2-dimethoxy-ethyl)-methyl-amide (1.0 equivalents) is suspended in toluene (5 volumes) and water (0.5 volumes) and trifluoroacetic acid is added keeping the temperature below 25° C. The resulting solution is allowed to stir for at least 8 hours below 25° C. and sampled for reaction completion. Once the reaction is deemed complete the solution is concentrated to an oil. The resulting oil is dissolved in brine (7.5 volumes) and water (2.5 volumes). Potassium carbonate is added portion wise to keep the temperature below 25° C. until a pH of 7.5 is achieved. The reaction is then washed with methylene chloride (3×10 volumes) and the combined organic layers are dried with sodium sulfate (200 wt %). The slurry is then filtered and the cake washed with methylene chloride (2×3 volumes). The resulting filtrate is held under vacuum for ≧24 hr., to concentrate the title preparation to a viscous amber oil (92% yield).

EXAMPLE 1

N-{2-[3'-(4-Methoxymethyl-phenyl)-2,3,5,6-tetrahydro-[1,2']bipyrazinyl-4-yl]-ethyl}-N-methyl-benzenesulfonamide hydrochloride

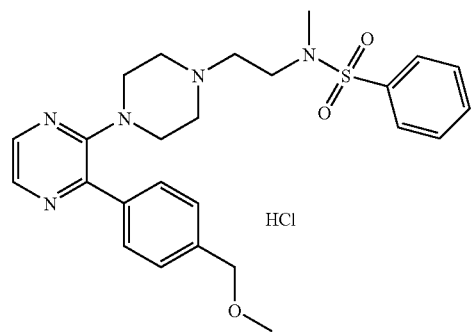

Dissolve benzenesulfonyl chloride (0.087 g, 0.49 mmol, 1.1 eq.) in dichloromethane (4 mL). Add {2-[3'-(4-methoxymethyl-phenyl)-2,3,5,6-tetrahydro-[1,2']bipyrazinyl-4-yl]-ethyl}-methyl-amine (0.150 g, 0.440 mmol, 1 eq.). Add morpholine, polymer-bound (0.201 g, 0.490 mmol, 1.1 eq.). Stir at room temperature for 2 hr. Purify by SCX chromatography (column washed with methanol and extracted with 7N NH₃/MeOH) to afford the free base of the title compound (0.202 g, 95% yield). MS (loop): m/z=482.3 [M+H].

Dissolve the free base (0.202 g, 0.42 mmol) in acetonitrile (2 mL) and water (4 mL). Add aqueous 1N HCl (1 eq., 0.42 mmol, 0.42 mL) and stir for 5 min. Lyophilize to afford the title compound (0.214 g, 98% yield). LC MS (ES): m/z=482.3 [M+H].

EXAMPLE 2

4-Fluoro-N-{2-[3'-(4-methoxymethyl-phenyl)-2,3,5,6-tetrahydro-[1,2']bipyrazinyl-4-yl]-ethyl}-N-methyl-benzenesulfonamide hydrochloride

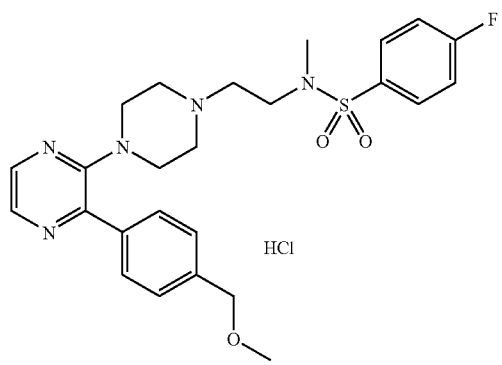

Dissolve 4-fluoro-benzenesulfonyl chloride (0.095 g, 0.49 mmol, 1.1 eq.) in dichloromethane (4 mL). Add {2-[3'-(4-methoxymethyl-phenyl)-2,3,5,6-tetrahydro-[1,2']bipyrazinyl-4-yl]-ethyl}-methyl-amine (0.150 g, 0.440 mmol, 1 eq.). Add morpholine, polymer-bound (0.201 g, 0.490 mmol, 1.1 eq.). Stir at room temperature for 2 hr. Purify by SCX chromatography (column washed with methanol and extracted with 7N NH₃/MeOH) to afford the free base of the title compound (0.220 g, 100% yield). MS (loop): m/z=500.0 [M+H].

Dissolve the free base (0.220 g, 0.44 mmol) in acetonitrile (2 mL) and water (4 mL). Add aqueous 1N HCl (1 eq., 0.44 mmol, 0.44 mL) and stir for 5 min. Lyophilize to afford the title compound (0.232 g, 98% yield). LC MS (ES): m/z=500.3 [M+H].

EXAMPLE 3

N-{2-[3'-(4-Fluoro-phenyl)-2,3,5,6-tetrahydro-[1,2'] bipyrazinyl-4-yl]-ethyl}-4-methoxy-N-methyl-benzenesulfonamide hydrochloride

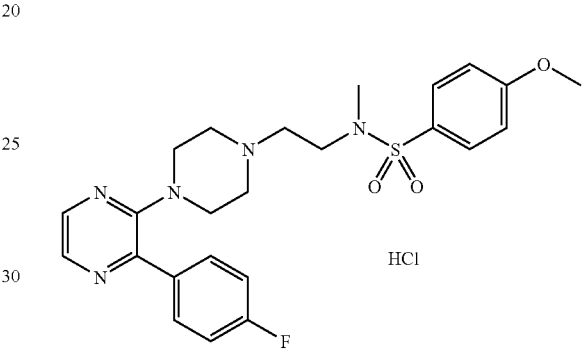

Dissolve 4-methoxy-benzenesulfonyl chloride (0.110 g, 0.530 mmol, 1.1 eq.) in dichloromethane (4 mL). Add {2-[3'-(4-fluoro-phenyl)-2,3,5,6-tetrahydro-[1,2']bipyrazinyl-4-yl]-ethyl}-methyl-amine (0.150 g, 0.480 mmol, 1 eq.). Add morpholine, polymer-bound (0.220 g, 0.530 mmol, 1.1 eq.). Stir at room temperature for 2 hr. Purify by SCX chromatography (column washed with methanol and extracted with 7N NH₃/MeOH) to afford the free base of the title compound (0.187 g, 80% yield). MS (loop): m/z=486.0 [M+H].

Dissolve the free base (0.187 g, 0.39 mmol) in acetonitrile (2 mL) and water (4 mL). Add aqueous 1N HCl (1 eq., 0.39 mmol, 0.39 mL). Stir for 5 min. and lyophilize to afford the title compound (0.192 g, 95% yield). LC MS (ES): m/z=486.3 [M+H].

EXAMPLE 4

4-Fluoro-N-{2-[3'-(4-fluoro-phenyl)-2,3,5,6-tetrahydro-[1,2']bipyrazinyl-4-yl]-ethyl}-N-methyl-benzenesulfonamide hydrochloride

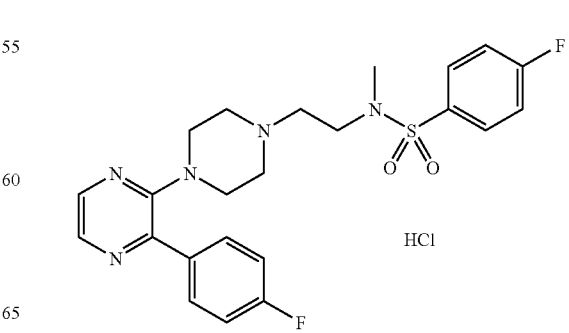

Prepare the title compound essentially according to the procedures from Example 3, using 4-fluoro-benzenesulfonyl chloride. (free base—77% yield, 0.174 g: MS (loop): m/z=474.0 [M+H]; salt formation—100% yield, 0.194 g: LC MS (ES): m/z=474.3 [M+H])

EXAMPLE 5

3,5-Difluoro-N-{2-[3'-(4-fluoro-phenyl)-2,3,5,6-tetrahydro-[1,2']bipyrazinyl-4-yl]-ethyl}-N-methyl-benzenesulfonamide hydrochloride

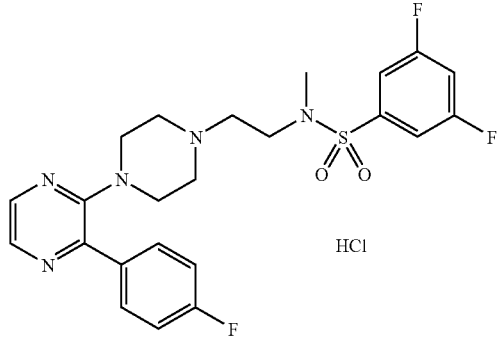

Prepare the title compound essentially according to the procedures in Example 3, using 3,5-difluoro-benzenesulfonyl chloride. Free base—84% yield, 0.197 g: MS (loop): m/z=492.0 [M+H]; salt formation—97% yield, 0.205 g, LC MS (ES): m/z=492.3 [M+H]).

EXAMPLE 6

2,4,6-Trifluoro-N-{2-[3'-(4-fluoro-phenyl)-2,3,5,6-tetrahydro-[1,2']bipyrazinyl-4-yl]-ethyl}-N-methyl-benzenesulfonamide hydrochloride

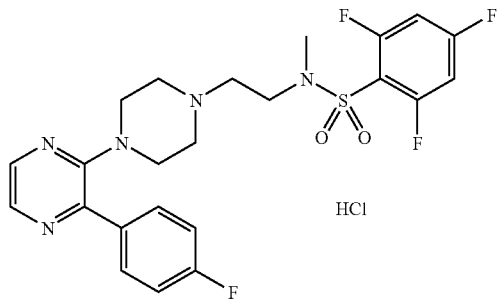

Dissolve 2,4,6-trifluoro-benzenesulfonyl chloride (0.120 g, 0.530 mmol, 1.1 eq.) in dichloromethane (4 mL). Add {2-[3'-(4-fluoro-phenyl)-2,3,5,6-tetrahydro-[1,2']bipyrazinyl-4-yl]-ethyl}-methyl-amine (0.150 g, 0.480 mmol, 1 eq.). Add morpholine, polymer-bound (0.220 g, 0.530 mmol, 1.1 eq.). Stir at room temperature for 2 hr. Purify by SCX chromatography (column washed with methanol and extracted with 7N NH$_3$/MeOH), normal phase chromatography with 10-20% MeOH/EtOAc and reverse phase chromatography to afford the free base (0.035 g, 14% yield). MS (loop): m/z=510.0 [M+H].

Convert the free base to the hydrochloride salt essentially as described in Example 3 to provide the title compound (86% yield, 0.032 g). LC MS (ES): m/z=510.0 [M+H].

EXAMPLE 7

1,2-Dimethyl-1H-imidazole-4-sulfonic acid {2-[3'-(4-methoxymethyl-phenyl)-2,3,5,6-tetrahydro-[1,2']bipyrazinyl-4-yl]-ethyl}-methyl-amide hydrochloride

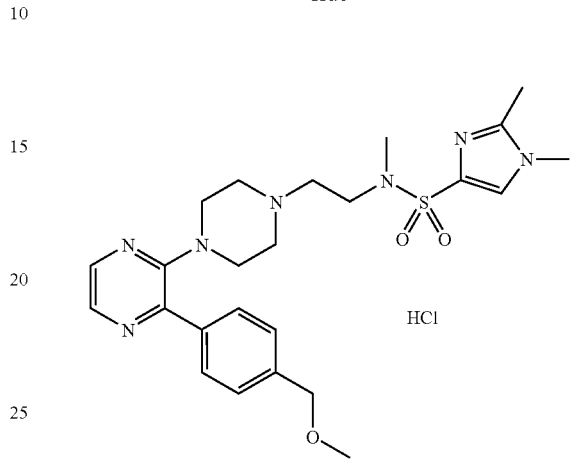

Dissolve 1,2-dimethyl-1H-imidazole-4-sulfonyl chloride (0.100 g, 0.49 mmol, 1.1 eq.) in dichloromethane (4 mL). Add {2-[3'-(4-methoxymethyl-phenyl)-2,3,5,6-tetrahydro-[1,2']bipyrazinyl]-ethyl}-methyl-amine (0.150 g, 0.440 mmol, 1 eq.). Add morpholine, polymer-bound (0.201 g, 0.490 mmol, 1.1 eq.). Stir at room temperature for 50 hr. Purify by SCX chromatography (column washed with MeOH and extracted with 7N NH$_3$/MeOH) and normal phase chromatography with 10-15% EtOAc/hexane to afford the free base of the title compound (0.063 g, 29% yield). MS (loop): m/z=500.0 [M+H].

Convert the free base to the hydrochloride salt essentially as described in Example 3 to provide the title compound.

EXAMPLE 8

N-{2-[3'-(4-Fluorophenyl)-2,3,5,6-tetrahydro-[1,2']bipyrazinyl-4-yl]-ethyl}-benzenesulfonamide hydrochloride

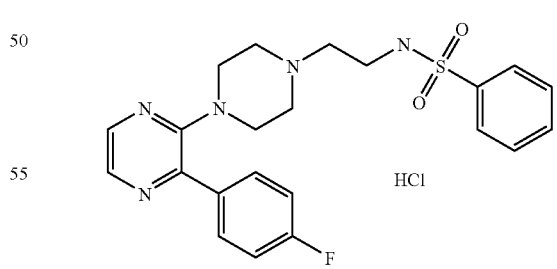

Dissolve 2-[3'-(4-fluorophenyl)-2,3,5,6-tetrahydro-[1,2']bipyrazinyl-4-yl]-ethylamine (0.099 g, 0.329 mmol) in dichloromethane (3 mL). Add resin-bound morpholine (0.145 g, 0.362 mmol) and shake at ambient temperature for 10 min. Add benzenesulfonyl chloride (0.064 g, 0.362 mmol)) and shake reaction at room temperature for 18 hr. Filter, concentrate and purify (SCX chromatography, followed by silica gel chromatography, eluting with 0:100 to 10:90 methanol:dichloromethane), to give free base of the title compound (109 mg, 75%). Dissolve the free base of the title compound (0.105 g, 0.238 mmol) in methanol and add a solution of ammonium chloride (0.013 g, 0.238 mmol) in a minimal volume of MeOH. Shake for 18 hr. at ambient temperature and concentrate to give the title compound (114 mg, 100%). MS (ES): m/z=442 [M+H]$^+$.

The compounds of Examples 9-13 may be prepared essentially as described in Example 8 using the appropriate amine and sulfonyl chloride.

| EX | Structure | Compound | MS (ES) [M + H] |
|---|---|---|---|
| 9 | 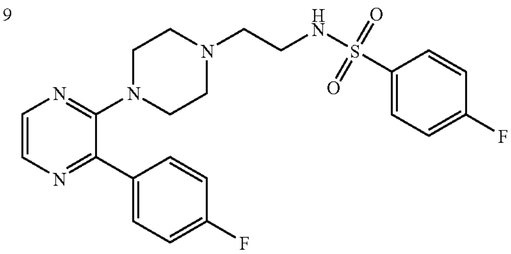 | 4-Fluoro-N-{2-[3'-(4-fluorophenyl)-2,3,5,6-tetrahydro-[1,2']bipyrazinyl-4-yl]-ethyl}-benzenesulfonamide | 460 |
| 10 | 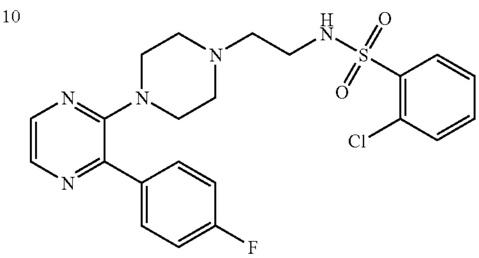 | 2-Chloro-N-{2-[3'-(4-fluorophenyl)-2,3,5,6-tetrahydro-[1,2']bipyrazinyl-4-yl]-ethyl}-benzenesulfonamide | 476 |
| 11 | 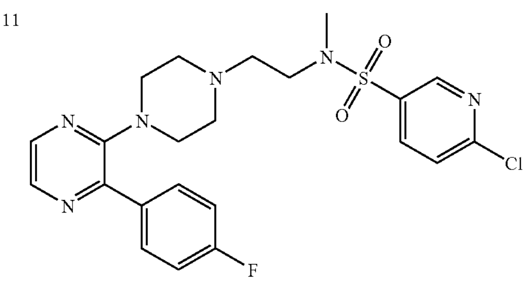 | 6-Chloropyridine-3-sulfonic acid {2-[3'-(4-fluorophenyl)-2,3,5,6-tetrahydro-[1,2']bipyrazinyl-4-yl]-ethyl}-methylamide | 491 |
| 12 | 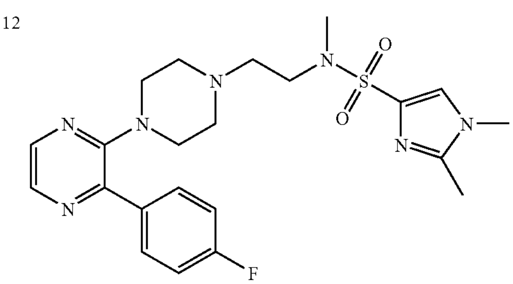 | 1,2-Dimethyl-1H-imidazole-4-sulfonic acid {2-[3'-(4-fluorophenyl)-2,3,5,6-tetrahydro-[1,2']bipyrazinyl-4-yl]-ethyl}-methylamide | 474 |
| 13 | 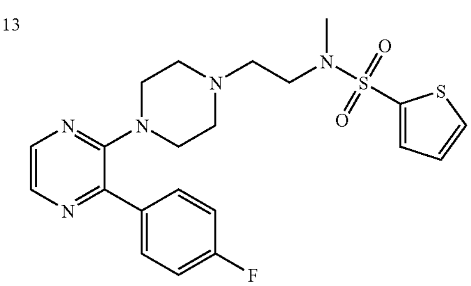 | Thiophene-2-sulfonic acid {2-[3'-(4-fluorophenyl)-2,3,5,6-tetrahydro-[1,2']bipyrazinyl-4-yl]-ethyl}-methylamide | 462 |

EXAMPLE 14

N-{2-[3'-(4-Fluorophenyl)-2,3,5,6-tetrahydro-[1,2']bipyrazinyl-4-yl]-ethyl}-N-methylbenzenesulfonamide hydrochloride

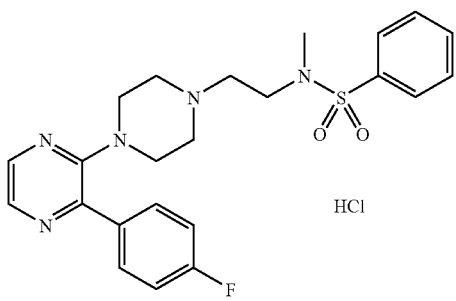

Dissolve N-{2-[3'-(4-fluorophenyl)-2,3,5,6-tetrahydro-[1,2']bipyrazinyl-4-yl]-2-oxoethyl}-N-methylbenzenesulfonamide (0.190 g, 0.405 mmol) in tetrahydrofuran (2.3 mL). Cool the reaction mixture in an ice bath and add 1 M borane-tetrahydrofuran complex (4.05 mL, 4.05 mmol) dropwise. Stir at room temperature for 18 hr. Quench with methanol, and concentrate. Dissolve in 1,2-dichloroethane (8 mL) and add ethylenediamine (400 µL). Reflux at 90° C. for 45 min. and then cool to room temperature. Add dichloromethane and water and separate layers. Extract aqueous layer three times with dichloromethane. Wash the combined organics with saturated aqueous sodium chloride, dry (magnesium sulfate), filter, concentrate and purify (silica gel chromatography, eluting with 1:1 to 100:0 ethyl acetate:hexanes), to give the free base of the title compound (50 mg, 27% yield).

Dissolve the free base (0.045 g, 0.099 mmol) in methanol and add a solution of ammonium chloride (0.005 g, 0.099 mmol) in a minimal volume of methanol. Shake for 18 hr. at ambient temperature and concentrate to give the title compound (49 mg, 100% yield). MS (ES): m/z=456 [M+H]$^+$.

EXAMPLE 15

2,3-Dimethyl-3H-imidazole-4-sulfonic acid {2-[3'-(4-fluoro-phenyl)-2,3,5,6-tetrahydro-[1,2']bipyrazinyl-4-yl]-ethyl}-methyl-amide hydrochloride

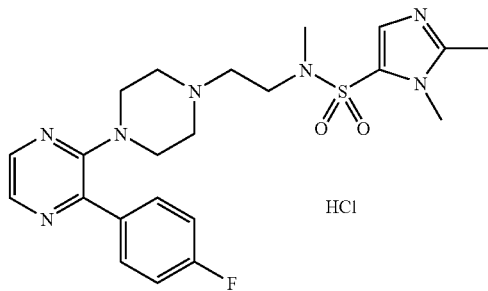

Dissolve {2-[3'-(4-fluoro-phenyl)-2,3,5,6-tetrahydro-[1,2']bipyrazinyl-4-yl]-ethyl}-methyl-amine (0.111 g, 0.352 mmol) in dichloromethane (4 mL). Add resin-bound morpholine (0.155 g, 0.387 mmol) followed by 1,2-dimethylimidazole-5-sulfonyl chloride (0.075 g, 0.387 mmol) and shake at ambient temperature for 72 hr. Filter, concentrate and purify (SCX chromatography, followed by silica gel chromatography, eluting with 100:0 to 0:100 hexanes:ethyl acetate, then 10:90 methanol:ethyl acetate, then 20:80 methanol:ethyl acetate) to give the free base of the title compound (118 mg, 71%).

Dissolve the free base (0.115 g, 0.243 mmol) in methanol and add a solution of ammonium chloride (0.013 g, 0.243 mmol) in a minimal volume of methanol. Shake for 18 hr. at ambient temperature and concentrate to give the title compound (124 mg, 100%). MS (ES): m/z=474 [M+H]$^+$.

EXAMPLE 16

1,2-Dimethyl-1H-imidazole-4-sulfonic acid {2-[3'-(2-fluoro-phenyl)-2,3,5,6-tetrahydro-[1,2']bipyrazinyl-4-yl]-ethyl}-methyl-amide hydrochloride

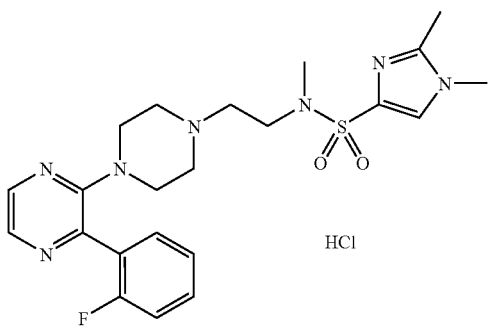

Dissolve {2-[3'-(2-fluoro-phenyl)-2,3,5,6-tetrahydro-[1,2']bipyrazinyl-4-yl]-ethyl}-methyl-amine (0.059 g, 0.190 mmol) in dichloromethane (5 mL). Add triethylamine (29 µL, 0.209 mmol) followed by 1,2-dimethyl-1H-imidazole-4-sulfonyl chloride (0.041 g, 0.209 mmol) and stir at ambient temperature for 72 hr. Concentrate under reduced pressure and purify (silica gel chromatography, eluting with 20:80 to 0:100 hexanes:ethyl acetate, then 10:90 methanol:ethyl acetate, then 20:80 methanol:ethyl acetate) to give the free base of the title compound (71 mg, 79%).

Dissolve the free base (0.069 g, 0.146 mmol) in methanol and add a solution of ammonium chloride (0.007 g, 0.146 mmol) in a minimal volume of methanol. Shake for 18 hr. at ambient temperature and concentrate to give the title compound (75 mg, 100%). MS (ES): m/z=474 [M+H]$^+$.

EXAMPLE 17

1-Methyl-1H-imidazole-4-sulfonic acid {2-[3'-(4-fluoro-phenyl)-2,3,5,6-tetrahydro-[1,2']bipyrazinyl-4-yl]-ethyl}-methyl-amide hydrochloride

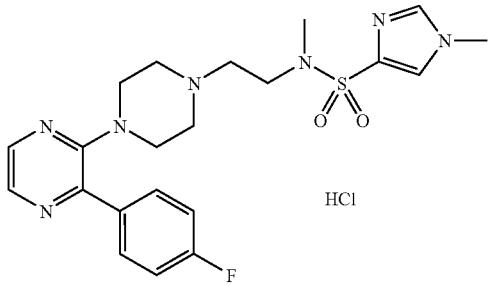

Dissolve {2-[3'-(4-fluoro-phenyl)-2,3,5,6-tetrahydro-[1,2']bipyrazinyl-4-yl]-ethyl}-methyl-amine (0.032 g, 0.101 mmol) in dichloromethane (5 mL). Add triethylamine (16 μL, 0.209 mmol) followed by 1-methyl-1H-imidazole-4-sulfonyl chloride (0.020 g, 0.112 mmol) and stir at ambient temperature for 72 hr. Concentrate under reduced pressure and purify (silica gel chromatography, eluting with 20:80 to 0:100 hexanes:ethyl acetate, then 10:90 methanol:ethyl acetate, then 20:80 methanol:ethyl acetate) to give the free base of the title compound (23 mg, 50%).

Dissolve the free base (0.020 g, 0.044 mmol) in methanol and add a solution of ammonium chloride (0.002 g, 0.044 mmol) in a minimal volume of methanol. Shake for 18 hr. at ambient temperature and concentrate to give the title compound (22 mg, 100%). MS (ES): m/z=460 [M+H]$^+$.

EXAMPLE 18

N-{2-[3'-(4-Hydroxymethyl-phenyl)-2,3,5,6-tetrahydro-[1,2']bipyrazinyl-4-yl]-ethyl}-N-methyl-benzenesulfonamide hydrochloride

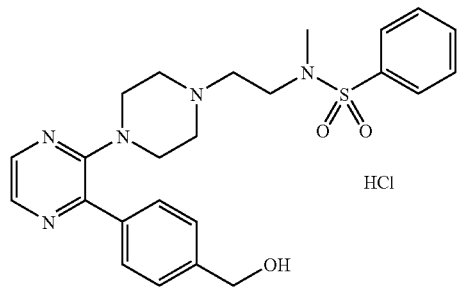

Combine N-[2-(3'-chloro-2,3,5,6-tetrahydro-[1,2']bipyrazinyl-4-yl)-ethyl]-N-methyl-benzenesulfonamide (0.300 g, 0.758 mmol), potassium carbonate (0.251 g, 1.82 mmol), (4-(hydroxymethyl)phenyl boronic acid (0.138 g, 0.909 mmol), and tetrakis(triphenylphosphine)palladium(0) (0.009 g, 0.008 mmol) in N,N-dimethylacetamide (1.5 mL). Add water (760 μL), and reflux reaction for 6 hr. Continue to heat at 70° C. for 18 hr. Add (4-(hydroxymethyl)phenyl boronic acid (0.069 g, 0.56 mmol) and tetrakis(triphenylphosphine)palladium(0) (0.009 g, 0.008 mmol) and heat to 115° C. for 6 hr. Continue to stir at ambient temperature over 72 hr. Add dichloromethane and wash with water. Extract the aqueous layer three times with dichloromethane. Dry the combined organic layers and purify (silica gel chromatography, eluting with 0:100 to 100:0 ethyl acetate:hexanes), to give the free base of the title compound (278 mg, 78%).

Dissolve the free base (0.268 g, 0.573 mmol) in acetonitrile (688 μL) and add aqueous 1 N HCl solution (688 μL, 0.688 mmol). Shake for 15 min. at ambient temperature. Freeze dry to give the title compound (290 mg, 100%). MS (ES): m/z=468 [M+H]$^+$.

EXAMPLE 19

1-Methyl-1H-pyrazole-4-sulfonic acid {2-[3'-(4-cyanomethyl-phenyl)-2,3,5,6-tetrahydro-[1,2']bipyrazinyl-4-yl]-ethyl}-methyl-amide hydrochloride

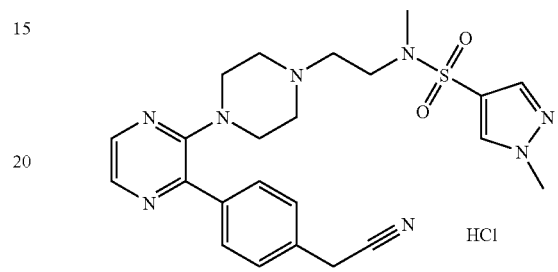

Dissolve 1-methyl-1H-pyrazole-4-sulfonic acid [2-(3'-chloro-2,3,5,6-tetrahydro-[1,2']bipyrazinyl-4-yl)-ethyl]-methyl-amide (0.250 g, 0.625 mmol) in DMA-H$_2$O (or DME:H$_2$O) (6 mL; 3:1 v/v, previously degassed with nitrogen). Add 4-cyanomethylphenyl boronic acid (0.121 g, 0.750 mmol), potassium carbonate (0.207 g, 1.500 mmol) and tetrakis(triphenylphosphine)palladium (0.036 g, 0.031 mmol). Stir the reaction mixture at 110° C. for 18 hr. Cool and dilute with ethyl acetate and water. Extract the aqueous layer with ethyl acetate and combine the organic layers. Dry the combined organic layers over sodium sulfate, filter, and concentrate. Purify by SCX chromatography, eluting with dichloromethane, dichloromethane:methanol 1:1, methanol, and 1N ammonia in methanol. Purify by silica gel chromatography eluting with hexanes:acetone 1:1 to afford the free base of the title compound (0.214 g, 71% yield).

Prepare the hydrochloride salt by dissolving the freebase (0.214 g) in acetonitrile and adding 1N aqueous hydrochloric acid (0.489 mL, 0.489 mmol). Stir for 1 hr. at room temperature. Remove the organics and lyophilize the remaining aqueous portion to afford the title compound (0.212 g). MS ES: m/z=481 [M+H]$^+$.

Prepare Examples 20 to 24 by essentially the same methods as described in Example 19 using the appropriate boronic acid or boronate ester.

| EX | Structure | Compound | yield (%) | MS (ES) [M + H] |
|---|---|---|---|---|
| 20 | 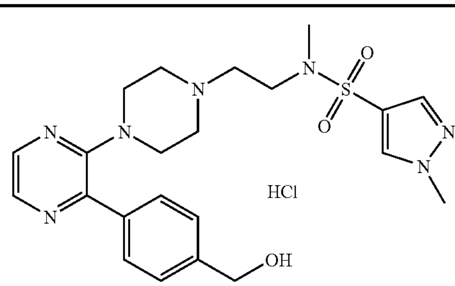 | 1-Methyl-1H-pyrazole-4-sulfonic acid {2-[3'-(4-hydroxymethyl-phenyl)-2,3,5,6-tetrahydro-[1,2']bipyrazinyl-4-yl]-ethyl}-methyl-amide hydrochloride | 77 | 472 |

| EX | Structure | Compound | yield (%) | MS (ES) [M + H] |
|---|---|---|---|---|
| 21 | 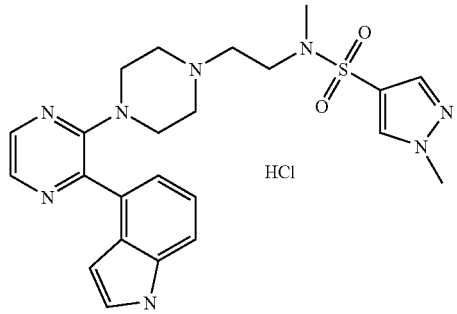 | 1-Methyl-1H-pyrazole-4-sulfonic acid {2-[3'-(1H-indol-4-yl)-2,3,5,6-tetrahydro-[1,2']bipyrazinyl-4-yl]-ethyl}-methyl-amide hydrochloride | 83 | 481 |
| 22 | 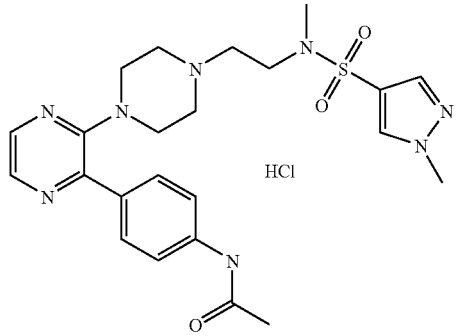 | N-[4-(4-{2-[Methyl-(1-methyl-1H-pyrazole-4-sulfonyl)-amino]-ethyl}-3,4,5,6-tetrahydro-2H-[1,2']bipyrazinyl-3'-yl)-phenyl]-acetamide hydrochloride | 91 | 499 |
| 23 | 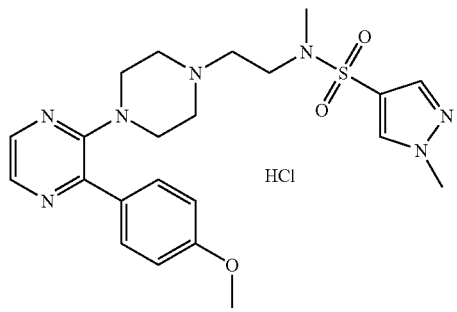 | 1-Methyl-1H-pyrazole-4-sulfonic acid {2-[3'-(4-methoxy-phenyl)-2,3,5,6-tetrahydro-[1,2']bipyrazinyl-4-yl]-ethyl}-methyl-amide hydrochloride | 90 | 472 |
| 24 | 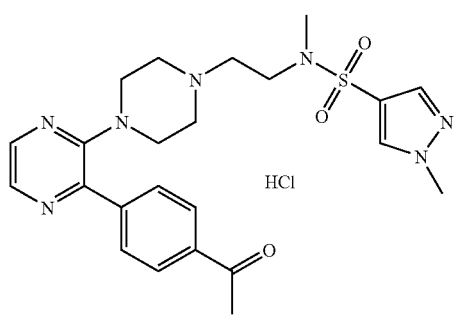 | 1-Methyl-1H-pyrazole-4-sulfonic acid {2-[3'-(4-acetyl-phenyl)-2,3,5,6-tetrahydro-[1,2']bipyrazinyl-4-yl]-ethyl}-methyl-amide hydrochloride | 90 | 484 |

EXAMPLE 25

1-Methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide hydrochloride

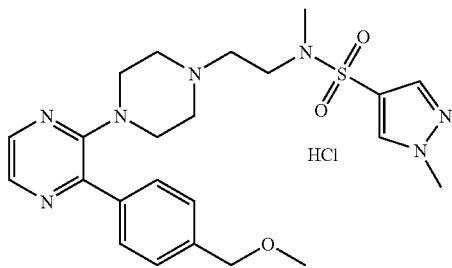

Cool a suspension of 3'-(4-methyoxymethyl-phenyl)-3,4,5,6-tetrahydro-2H-[1,2']bipyrazinyl dihydrochloride (23.62 g, 66.11 mmol) in 1,2-dichloroethane (500 mL) at 5° C. Treat with 1.0 M NaOH (141 mL, 141 mmol), separate layers, dry the organics over $Na_2SO_4$, filter, then add to a solution of 1-methyl-1H-pyrazole-4-sulfonic acid methyl-(2-oxo-ethyl)-amide (17.66 g, 81.29 mmol) in 1,2-dichloroethane (1 L). Cool the reaction mixture to 5-10° C., treat with sodium triacetoxyborohydride (29.50 g, 132.2 mmol), and stir at room temperature overnight. Recool the reaction to 5° C., treat with 5 M NaOH (200 mL), and separate the resulting layers. Extract the aqueous layer with $CH_2Cl_2$ (500 mL), combine the organics, dry over $Na_2SO_4$, filter and concentrate. Dissolve the crude material in MeOH/EtOAc, treat with activated carbon (50 g) at room temperature for 1 hr., then filter through celite and concentrate to provide the free base of the title compound as an oil (29.8 g, 93%). Cool anhydrous EtOH (100 mL) to 5° C. and then add dropwise acetyl chloride (4.45 mL, 61.39 mmol). Stir the resulting solution at room temperature for about 15 min., then add it dropwise to a solution of the above free base dissolved in anhydrous EtOH (800 mL). Stir at room temperature for 0.5 hr., then concentrate in vacuo to ca. 20% of the original volume. Treat the resulting oil/solid with EtOAc (1.5 L). Recover the resulting yellow solid by vacuum filtration and dry in vacuo to provide the title compound (27.28 g, 85.2%). MS ES: m/z=486 $[M+H]^+$.

Alternatively, the free base of the title compound may be made as follows. Suspend 3'-(4-Methoxymethyl-phenyl)-3,4,5,6-tetrahydro-2H-[1,2']bipyrazinyl (1.0 equivalents) and 1-methyl-1H-pyrazole-4-sulfonic acid methyl-(2-oxo-ethyl)-amide (1.1 equivalents) in 2-methyltetrahydrofuran (10 volumes) and stir for at least 30 min., until complete imine formation. Add the solution to a slurry of sodium triacetoxyborohydride (1.5 equivalents) in 2-methyltetrahydrofuran (5 volumes) portion-wise to keep the temperature below 25° C. Stir the resulting slurry for at least 30 min., until reaction completion. Add 1 N sodium hydroxide (10 volumes), keeping the temperature below 25° C. Stirring for at least 30 min, until reaction completion, allow the phases to settle for at least 30 min. and then separate the phases. Wash the organic layer with 1 N NaOH (5 volumes) and water (1 volume). Heat the organic layer and displace the solvent with 2-propanol until the final volume of 2-propanol is 5 volumes based on theoretical 1-methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide. Cool the reaction to 50° C. over at least 30 min. and seed with crystals of 1-methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide (1 wt %). After holding at 50° C. for at least 60 minutes the resulting slurry is cooled to 20° C. over at least 60 min. Allow granulation of the slurry at 20° C. for at least 60 min. Wash the resulting solids with 2-propanol (2×3 volumes). Dry the cake at 50° C. under vacuum with nitrogen bleed for at least 12 hr. to obtain 1-methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide as a pale-yellow solid (70% yield).

EXAMPLE 26

1-Methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide tartrate 1-Methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide (1.0 equivalents) and L-tartaric acid (0.95 equivalents) is suspended in 2B3 EtOH (10 volumes) and heated to at least 75° C. for at least 60 min. The resulting slurry is then cooled to 20° C. over at least 90 min. After granulating at 20° C. for at least 60 min., the resulting solids are filtered and washed with 2B3 EtOH (2×3 volumes). The cake is then dried at 50° C. under vacuum with nitrogen bleed for at least 12 hr. 1-Methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide L-tartrate is isolated as an off-white solid (92% yield). m.p. 161° C.

EXAMPLE 27

1-Methyl-1H-pyrazole-4-sulfonic acid methyl-{2-[3'-(4-pyrazol-1-ylmethyl-phenyl)-2,3,5,6-tetrahydro-[1,2']bipyrazinyl-4-yl]-ethyl}-amide hydrochloride

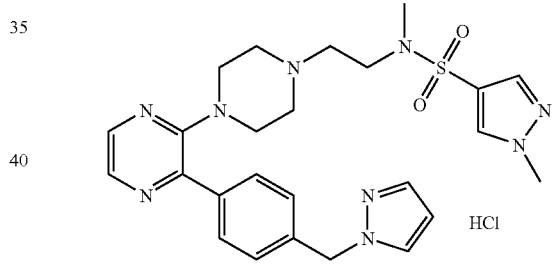

Dissolve 1H-pyrazole (2.401 mmol, 0.163 g) in dimethylformamide (5 mL) at room temperature under nitrogen. Add sodium hydride (2.401 mmol, 0.096 g, 60% dispersion in mineral oil). Stir the mixture for 30 min. at room temperature. Add methanesulfonic acid 4-(4-{2-[methyl-(1-methyl-1H-pyrazole-4-sulfonyl)-amino]-ethyl}-3,4,5,6-tetrahydro-2H-[1,2']bipyrazinyl-3'-yl)-benzyl ester (0.600 mmol, 0.330 g) as a solution in dimethylformamide (5 mL). Stir at room temperature overnight. Dilute with water and ethyl acetate. Separate and extract the aqueous phase with ethyl acetate. Combine the organic phases, wash with water, brine, water, and then brine. Separate and dry the organic phase over sodium sulfate, filter, concentrate and purify by silica gel chromatography, eluting with dichloromethane:2N ammonia in methanol 9:1 to afford the free base with minor impurities. Filter the mixture through SCX resin with dichloromethane, dichloromethane:methanol 1:1, methanol, followed by 1N ammonia in methanol. Combine fractions with the desired product, concentrate, and pass through a silica gel plug eluting with dichloromethane:methanol 4:1 to afford the free base of the title compound (0.156 g). Prepare the hydrochloride salt by dissolving the free base in acetone (2 mL) and then adding with stirring 1M HCl in ether (0.359 mL, 0.359 mmol). Wash the resulting precipitate with diethyl ether to afford the title compound (0.160 g, 48% yield). MS ES: m/z=522 $[M+H]^+$.

Prepare Examples 28 and 29 using essentially the same methods as described in Example 27 using 1H-1,2,3-triazole.

| EX | Structure | Compound | yield (%) | MS (ES) [M + H] |
|---|---|---|---|---|
| 28 | 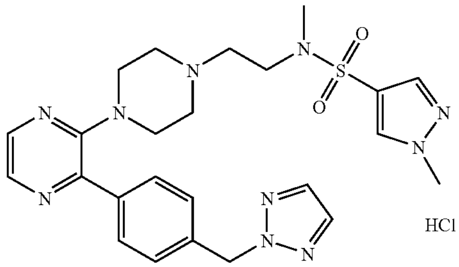 | 1-Methyl-1H-pyrazole-4-sulfonic acid methyl-{2-[3'-(4-[1,2,3]triazol-2-ylmethyl-phenyl)-2,3,5,6-tetrahydro-[1,2']bipyrazinyl-4-yl]-ethyl}-amide hydrochloride | 23 | 523 |
| 29 | 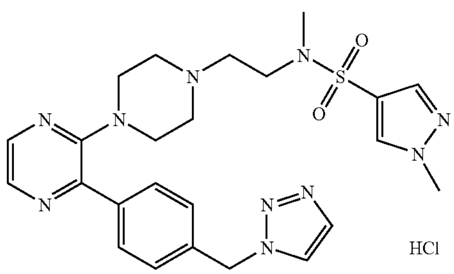 | 1-Methyl-1H-pyrazole-4-sulfonic acid methyl-{2-[3'-(4-[1,2,3]triazol-1-ylmethyl-phenyl)-2,3,5,6-tetrahydro-[1,2']bipyrazinyl-4-yl]-ethyl}-amide hydrochloride | 56 | 523 |

EXAMPLE 30

1,3-Dimethyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide hydrochloride

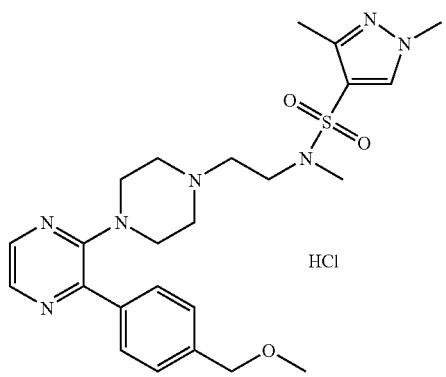

Dissolve 1,3-dimethyl-1H-pyrazole-4-sulfonic acid [2-(3'-chloro-2,3,5,6-tetrahydro-[1,2']bipyrazinyl-4-yl)-ethyl]-methyl-amide (270 mg, 0.652 mmol) in DMA-H$_2$O (10 ml; 3:1 v/v, previously degassed with nitrogen). Add 4-methoxymethylphenyl boronic acid (130 mg, 0.783 mmol), potassium carbonate (216 mg, 1.56 mmol) and tetrakis(triphenylphosphine)palladium (38 mg, 0.0326 mmol). Heat the reaction mixture at 110° C. for 18 hr. Cool and dilute with ethyl acetate and water. Extract the aqueous layer with ethyl acetate and combine the organic layers. Wash the organic layers with brine and concentrate. Purify by chromatography, eluting with 1:2 hexanes:acetone to afford the free base of the title compound (182 mg, 56% yield) as a white foam.

Prepare the hydrochloride salt by dissolving the free base (182 mg) in acetonitrile and adding 1N aqueous HCl (0.401 ml, 0.401 mmol). Stir for 1 hr. at ambient temperature. Remove the organics and lyophilize the remaining aqueous portions to afford the title compound (100% yield). MS ES: m/z=500 [M+H]$^+$.

Prepare Examples 31-33 using essentially the same methods as described in Example 30 using the appropriate boronic acid.

| EX | Structure | Compound | Yield (%) | MS (ES) [M + H] |
|---|---|---|---|---|
| 31 | 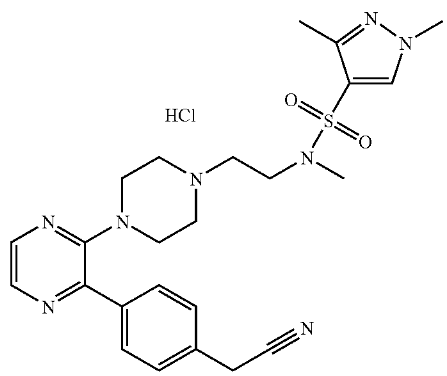 | 1,3-Dimethyl-1H-pyrazole-4-sulfonic acid {2-[3'-(4-cyanomethyl-phenyl)-2,3,5,6-tetrahydro-[1,2']bipyrazinyl-4-yl]-ethyl}-methyl-amide hydrochloride | 47 | 495 |
| 32 | 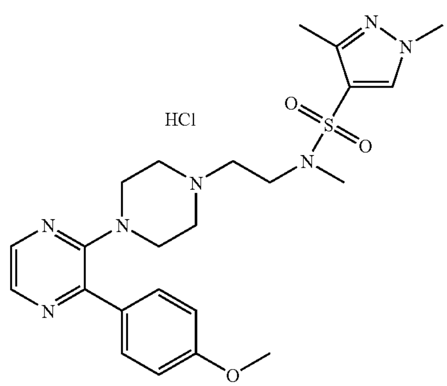 | 1,3-Dimethyl-1H-pyrazole-4-sulfonic acid {2-[3'-(4-methoxy-phenyl)-2,3,5,6-tetrahydro-[1,2']bipyrazinyl-4-yl]-ethyl}-methyl-amide hydrochloride | 75 | 486 |
| 33 | 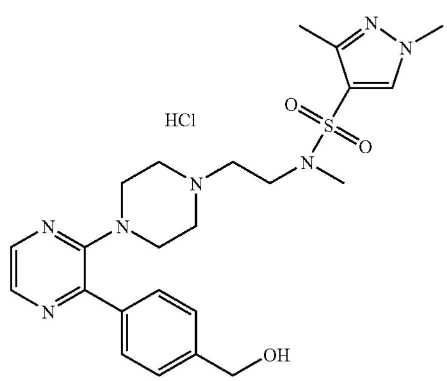 | 1,3-Dimethyl-1H-pyrazole-4-sulfonic acid {2-[3'-(4-hydroxymethyl-phenyl)-2,3,5,6-tetrahydro-[1,2']bipyrazinyl-4-yl]-ethyl}-methyl-amide hydrochloride | 76 | 486 |

EXAMPLE 34

N-[4-(4-{2-[Methyl-(1-methyl-1H-pyrazole-4-sulfonyl)-amino]-ethyl}-3,4,5,6-tetrahydro-2H-[1,2']bipyrazinyl-3'-yl)-benzyl]-acetamide hydrochloride

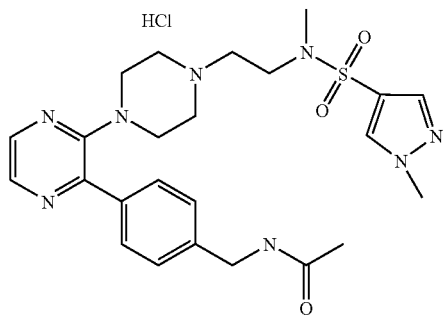

Dissolve 1-methyl-1H-pyrazole-4-sulfonic acid [2-(3'-chloro-2,3,5,6-tetrahydro-[1,2']bipyrazinyl-4-yl)-ethyl]-methyl-amide (200 mg, 0.483 mmol) in DMA-H$_2$O (10 ml; 3:1 v/v, previously degassed with nitrogen). Add 4-acetamidophenyl boronic acid (112 mg, 0.580 mmol), potassium carbonate (160 mg, 1.16 mmol) and tetrakis(triphenyl-phosphine)palladium (28 mg, 0.024 mmol). Heat the reaction mixture at 110° C. for 18 hr. Cool and dilute with ethyl acetate and water. Extract the aqueous layer with ethyl acetate and combine the organic layers. Wash the combined organic layers with brine and concentrate. Purify by chromatography, eluting with 1:2 hexanes:acetone to afford the free base of the title compound (124 mg, 50% yield) as a white foam.

Prepare the hydrochloride salt by dissolving the free base (124 mg) in acetonitrile and adding 1N aqueous HCl (0.266 ml, 0.266 mmol). Stir for 1 hr at ambient temperature. Remove the organics and lyophilize the remaining aqueous portions to afford the title compound (100% yield). MS ES: m/z=513 [M+H]$^+$.

EXAMPLE 35

Pyridine-3-sulfonic acid {2-[3'-(4-fluoro-phenyl)-2,3,5,6-tetrahydro-[1,2']bipyrazinyl-4-yl]-ethyl}-methyl-amide hydrochloride

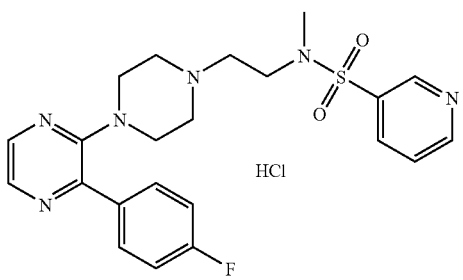

Dissolve pyridine-3-sulfonic acid [2-(3'-chloro-2,3,5,6-tetrahydro-[1,2']bipyrazinyl-4-yl)-ethyl]-methyl-amide (0.200 g, 0.504 mmol) in DMA-H$_2$O (4 mL; 3:1 v/v, previously degassed with nitrogen). Add 4-fluorophenyl boronic acid (0.084 g, 0.605 mmol), potassium carbonate (0.167 g, 1.209 mmol) and tetrakis(triphenyl-phosphine)palladium (0.029 g, 0.025 mmol). Stir the reaction mixture at 110° C. for 18 hr. Cool and dilute with ethyl acetate and water. Extract the aqueous layer with ethyl acetate and combine the organic layers. Dry the organics over sodium sulfate, filter, and concentrate. Purify by SCX chromatography, eluting with dichloromethane, dichloromethane:methanol, methanol, and 1N ammonia in methanol. Purify by silica gel chromatography eluting with hexanes:acetone 1:1 to afford the free base of the title compound (0.136 g, 59% yield).

Prepare the hydrochloride salt by dissolving freebase (0.136 g) in acetonitrile and adding 1N aqueous hydrochloric acid (0.626 mL, 0.626 mmol). Stir for 1 hr. at room temperature. Remove the organics and lyophilize the remaining aqueous portion to afford the title compound (0.138 g, 56% yield). MS ES: m/z=457 [M+H]$^+$.

EXAMPLE 36

Pyridine-2-sulfonic acid {2-[3'-(4-fluoro-phenyl)-2,3,5,6-tetrahydro-[1,2']bipyrazinyl-4-yl]-ethyl}-methyl-amide hydrochloride

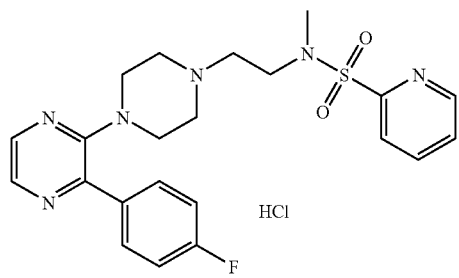

Prepare the title compound using essentially the same methods as described in Example 34 using pyridine-3-sulfonic acid [2-(3'-chloro-2,3,5,6-tetrahydro-[1,2']bipyrazinyl-4-yl)-ethyl]-methyl-amide (89% yield). MS (ES): m/z=457 [M+H]

EXAMPLE 37

1-Methyl-1H-pyrazole-4-sulfonic acid (2-{4-[2-(4-methoxymethyl-phenyl)-pyridin-3-yl]-piperazin-1-yl}-ethyl)-methyl-amide hydrochloride

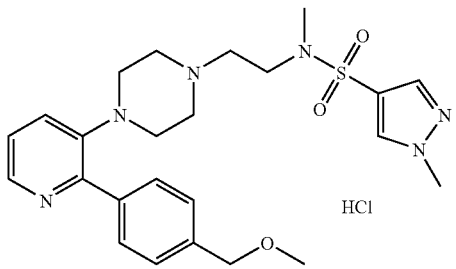

Dissolve 1-methyl-1H-pyrazole-4-sulfonic acid {2-[4-(2-chloro-pyridin-3-yl)-piperazin-1-yl]-ethyl}-methyl-amide (0.200 g, 0.501 mmol) in DME-H$_2$O (6 mL; 3:1 v/v, previously degassed with nitrogen). Add 4-(methoxymethyl)boronic acid (0.125 g, 0.752 mmol), potassium carbonate (0.166 g, 1.203 mmol) and tetrakis(triphenylphosphine)-palladium (0.029 g, 0.025 mmol). Heat the reaction mixture at 80° C. for 8 hr. Cool to room temperature and concentrate to remove DME. Dilute with ethyl acetate and brine. Extract the aqueous layer with ethyl acetate. Combine the organic phases, dry over sodium sulfate, filter, and concentrate. Purify by silica gel chromatography eluting with dichloromethane:methanol 94:6 to 90:10 to afford the freebase of the title compound with minor impurities. Purify by SCX eluting sequentially with dichloromethane, dichloromethane:methanol 1:1, methanol, and 1N ammonia in methanol. Pass the pure free base through a silica gel plug eluting with dichloromethane:methanol 4:1 to afford the free base of the title compound.

Prepare the hydrochloride salt by dissolving the free base (0.193 g) in acetone and adding 1N HCl in diethyl ether (0.438 mL, 0.438 mmol). Stir for 20 min. at room temperature and then add diethyl ether to precipitate the salt. Wash the salt with diethyl ether to afford the title compound (0.181 g, 69% yield). MS ES: m/z=485 [M+H]$^+$.

Prepare Examples 38 to 40 using essentially the same methods described in Example 37 using the appropriate boronic acid.

| EX | Structure | Compound | yield (%) | MS (ES) [M + H] |
|---|---|---|---|---|
| 38 | 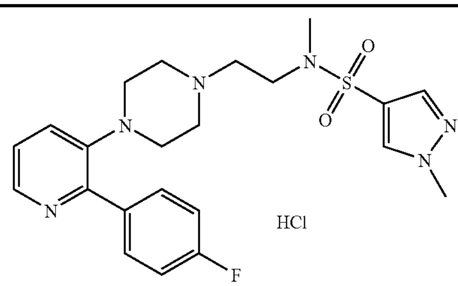 | 1-Methyl-1H-pyrazole-4-sulfonic acid (2-{4-[2-(4-fluoro-phenyl)-pyridin-3-yl]-piperazin-1-yl}-ethyl)-methyl-amide hydrochloride | 92 | 459 |
| 39 | 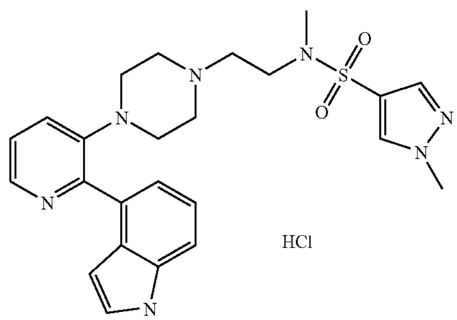 | 1-Methyl-1H-pyrazole-4-sulfonic acid (2-{4-[2-(1H-indol-4-yl)-pyridin-3-yl]-piperazin-1-yl}-ethyl)-methyl-amide hydrochloride | 78 | 480 |
| 40 | 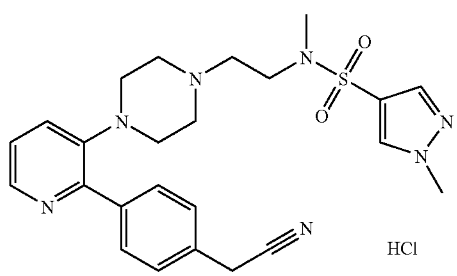 | 1-Methyl-1H-pyrazole-4-sulfonic acid (2-{4-[2-(4-cyanomethyl-phenyl)-pyridin-3-yl]-piperazin-1-yl}-ethyl)-methyl-amide hydrochloride | 62 | 480 |

EXAMPLE 41

4-Fluoro-N-(2-{4-[2-(1H-indol-4-yl)-pyridin-3-yl]-piperazin-1-yl}-ethyl)-N-methyl-benzenesulfonamide hydrochloride

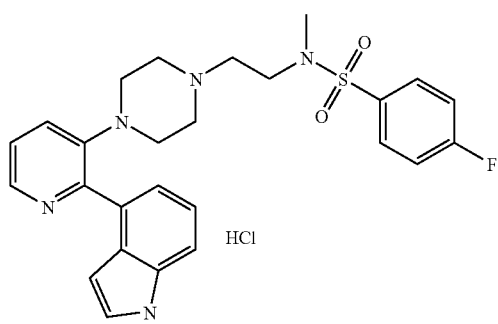

Dissolve N-{2-[4-(2-chloro-pyridin-3-yl)-piperazin-1-yl]-ethyl}-4-fluoro-N-methyl-benzenesulfonamide (0.160 g, 0.387 mmol) in DME (5 mL, previously degassed with nitrogen). Add 4-indole boronic acid (0.094 g, 0.581 mmol), 2N aqueous potassium carbonate (0.464 mL, 0.129 g, 0.930 mmol), and tetrakis(triphenylphosphine)palladium (0.022 g, 0.022 mmol). Stir the reaction mixture at 80° C. for 18 hr. Add fresh catalyst (0.015 g) and boronic acid (0.050 g). Stir an additional 8 hr. at 95° C. Cool to room temperature and concentrate to remove DME. Dilute with ethyl acetate and brine. Extract the aqueous layer with ethyl acetate. Combine the organic layers, dry over sodium sulfate, filter, and concentrate. Purify the resulting material by silica gel chromatography eluting with dichloromethane:methanol 94:6 to 90:10 to afford the title compound (0.031 g).

Prepare the hydrochloride salt by dissolving the free base (0.031 g) in acetone (2 mL) and adding 1N HCl in diethyl ether (0.069 mL, 0.069 mmol). Stir for 20 min. at room temperature and then add diethyl ether to precipitate the salt. Wash the salt with diethyl ether to afford the title compound (0.036 g, 18% yield). MS ES: m/z=494 [M+H]$^+$.

EXAMPLE 42

4-Fluoro-N-(2-{4-[2-(4-methoxymethyl-phenyl)-pyridin-3-yl]-piperazin-1-yl}-ethyl)-N-methyl-benzenesulfonamide hydrochloride

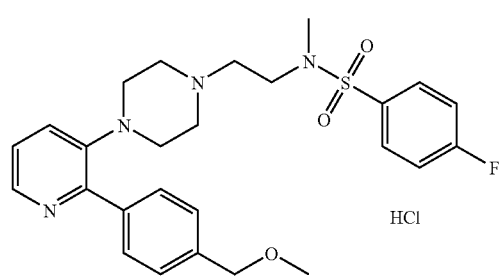

Dissolve N-{2-[4-(2-chloro-pyridin-3-yl)-piperazin-1-yl]-ethyl}-4-fluoro-N-methyl-benzenesulfonamide (0.160 g, 0.387 mmol) in DME (5 mL, previously degassed with nitrogen). Add 4-(methoxymethyl)boronic acid (0.096 g, 0.581 mmol), 2N aqueous potassium carbonate (0.464 mL, 0.129 g, 0.930 mmol), and tetrakis(triphenylphosphine)-palladium (0.022 g, 0.022 mmol). Stir the reaction mixture at 80° C. for 18 hr. Increase the temperature to 95° C. and stir an additional 8 hr. Add fresh catalyst (0.015 g) and boronic acid (0.050 g). Stir 18 hr. at 95° C. Cool to room temperature and concentrate to remove DME. Dilute with ethyl acetate and brine. Extract the aqueous layer with ethyl acetate. Combine the organic phases, dry over sodium sulfate, filter, and concentrate. Purify by silica gel chromatography eluting with dichloromethane:methanol 98:2 to 90:10 to afford the free base of the title compound (0.075 g). Prepare the hydrochloride salt by dissolving the free base (0.075 g) in acetone (2 mL) and adding 1N HCl in diethyl ether (0.165 mL, 0.165 mmol). Stir for 20 min. at room temperature and then add diethyl ether to precipitate the salt. Wash the salt with diethyl ether and dry to afford the title compound (0.079 g, 38% yield). MS ES: m/z=499 [M+H]$^+$.

EXAMPLE 43

N-{4-[3-(4-{2-[Methyl-(1-methyl-1H-pyrazole-4-sulfonyl)-amino]-ethyl}-piperazin-1-yl)-pyridin-2-yl]-phenyl}-acetamide dihydrochloride

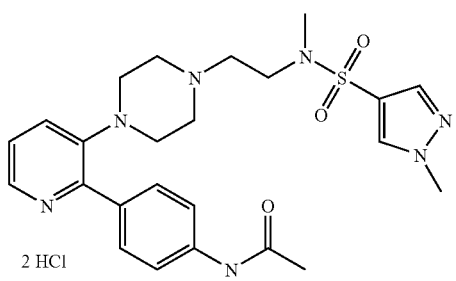

Dissolve 1-methyl-1H-pyrazole-4-sulfonic acid {2-[4-(2-chloro-pyridin-3-yl)-piperazin-1-yl]-ethyl}-methyl-amide (230 mg, 0.58 mmol) in DMA-H$_2$O (6 mL; 5:1 v/v, previously degassed with nitrogen). Add 4'-(4,4,5,5-tetramethyl-1,3,2-dioxaborolan-2-yl)acetanilide (181 mg, 0.69 mmol), potassium carbonate (191 mg, 1.38 mmol) and tetrakis(triphenylphosphine)palladium (33 mg, 0.03 mmol). Heat the reaction mixture at 110° C. for 18 hr. Cool and dilute with ethyl acetate and water. Extract the aqueous layer with ethyl acetate and combine the organic layers. Wash the combined organic layers with brine and concentrate. Purify by chromatography, eluting with 1:2 hexanes:acetone to afford the free base of the title compound (228 mg, 79% yield) as a white solid.

Prepare the dihydrochloride salt by dissolving the free base (182 mg) in acetonitrile and adding 1N aqueous HCl (0.962 ml, 0.962 mmol). Stir for 1 hr at ambient temperature. Remove the organics and lyophilize the remaining aqueous portions to afford the title compound (100% yield). MS ES: m/z=498 [M+H]$^+$.

EXAMPLE 44

1-Methyl-1H-pyrazole-4-sulfonic acid (2-{4-[2-(4-methoxy-phenyl)-pyridin-3-yl]-piperazin-1-yl}-ethyl)-methyl-amide hydrochloride

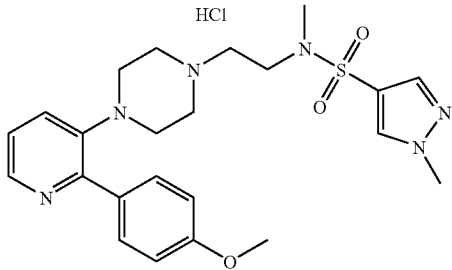

Prepare the title compound using essentially the same methods as described in Example 43 using 4-(methoxy)boronic acid. (85% yield). MS (ES): m/z=471 [M+H]

EXAMPLE 45

1-Methyl-1H-pyrazole-4-sulfonic acid methyl-(2-{4-[2-(4-pyrazol-1-ylmethyl-phenyl)-pyridin-3-yl]-piperazin-1-yl}-ethyl)-amide dihydrochloride

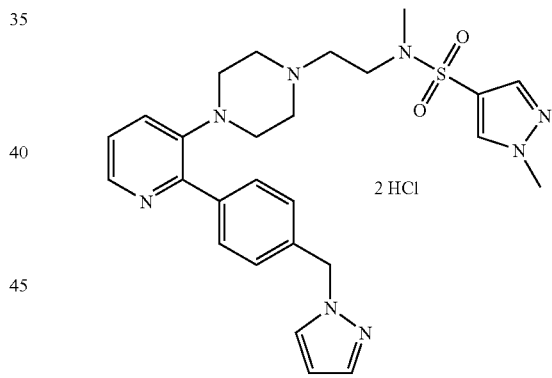

Dissolve 1-methyl-1H-pyrazole-4-sulfonic acid (2-{4-[2-(4-hydroxymethyl-phenyl)-pyridin-3-yl]-piperazin-1-yl}-ethyl)-methyl-amide (244 mg, 0.52 mmol) in dry dichloromethane (5 mL) and cool in an ice bath. Add triethylamine (108 µL, 0.78 mmol) and methanesulfonyl chloride (44 µL, 0.57 mmol) and stir for 1 hr. Dilute with dichlormethane and add saturated aqueous sodium bicarbonate solution. Separate the organic layer and wash with brine and dry over sodium sulfate. Filter and evaporate to afford the crude mesylate (284 mg, 100%) which may be used without further purification.

Add sodium hydride (83 mg of a 60% wt/wt suspension in oil, 2.07 mmol) to a solution of 1H-pyrazole (141 mg, 2.07 mmol) in dry dimethylformamide (1 mL) in an ice-bath and allow to stir for 30 min. Then add dropwise a solution of the above prepared mesylate (84 mg, 0.52 mmol) in dry dimethylformamide (3 mL) and allow the reaction to warm to ambient temperature and stir for 18 hr. Partition the mixture between ethyl acetate and aqueous sodium bicarbonate solution. Separate the organics and dry over sodium sulfate. Purify by flash chromatography on silica gel eluting with 1:1 to 2:1 acetone-hexanes to afford a product which is then re-purified by reverse-phase chromatography. Remove the solvent and lyophilize to afford the free base of the title compound. (55 mg, 20% yield) as a white foam.

Prepare the dihydrochloride salt by dissolving the free base (55 mg) in acetonitrile and adding 1N aqueous HCl (0.222 mL, 0.222 mmol). Stir for 1 hr. at ambient temperature. Remove the organics and lyophilize the remaining aqueous portions to afford the title compound (100% yield). MS ES: m/z=521 [M+H]$^+$.

The 5-HT$_7$ receptor antagonists of the present invention are relatively selective for the 5-HT$_7$ receptor. The compounds of the present invention are particularly relatively selective for the 5-HT$_7$ receptor in comparison to other 5-HT receptor subtypes and specifically the 5-HT$_{1A}$, 5-HT$_{1B}$ and 5-HT$_{1D}$ receptors. This selectivity is demonstrated in the following receptor binding assays and receptor antagonist activity assays.

Membrane Preparation:

Membranes for affinity and antagonist activity assays are prepared essentially as follows. AV-12 cells, stably expressing the 5-HT$_7$ receptor, are grown as a monolayer in 5×T-150 flasks in DMEM/F12 (3:1) 5% FBS, 20 mM HEPES, 400 mg/mL geneticin, 50 mg/mL tobramycin. After growing to 90% confluence the media is removed and replaced with Hybritech media (a low calcium version of DMEM/F12 media having 11 mg/L calcium) containing 2% horse serum, 100 mg/mL dextran sulfate, 1 mg/mL nucellin, 1 mg/mL human transferrin (partially iron saturated), 50 mg/mL tobramycin, 20 mM HEPES, 100 mg/mL geneticin, 0.04% pluronic F68. The cells are grown overnight to condition the media. The next morning the conditioned media (~150 mL total) is removed and set aside in a sterile container. The cells are trypsinized and collected in the conditioned media. Fresh suspension media is added to bring the total volume to 500 mL and a cell density of 5×10$^5$ cells/mL. The suspension culture volume is repeatedly increased over the next 3 weeks to the desired volume and density until harvest (approx. 3.5-4.0×10$^6$ cells per mL targeted cell density). Cells are harvested by centrifugation at 1,500 g at 4° C. for 30 min. The supernatant is decanted and the cell pellets are resuspended in ice-cold phosphate buffered saline (PBS). The cell suspension is aliquoted into 50 mL centrifuge tubes and centrifuged at 1,500 g at 4° C. for 15 min. The supernatant is removed, the pellets are weighed, and then frozen on dry ice.

To prepare membranes, the above pellets are resuspended in ice-cold Tris buffer (20 mM Tris HCl, pH 7.4 at 23° C., 5 mM EDTA) and homogenized with a Wheaton tissue grinder. The lysate is subsequently centrifuged at 200×g for 5 min. at 4° C. to pellet large fragments which are discarded. The supernatant is collected and centrifuged at 40,000×g for 60 min. at 4° C. The resulting pellet is resuspended in a final buffer containing 50 mM Tris HCl and 0.5 mM EDTA, pH 7.4. Membrane preparations are snap-frozen on dry ice and stored at −80° C. Protein concentrations are determined by the method of Bradford. *Anal. Biochem.*, 72:248-254, 1976.

For cAMP functional assays, the 5-HT$_7$-expressing cells from above are grown in 150 cm$^2$ flasks and processed essentially as follows. The media is aspirated from the flasks and cells are washed with 1 mL PBS. The cells are released from monolayer with enzyme free cell dissociation solution (Specialtymedia CAT#S-004-B, www.Chemicon.com) and resuspended in complete media. A sample of the cells is counted and the remainder is centrifuged as above for 3 min. The resulting cell pellet is resuspended in PBS at a concentration of 1×10$^6$ cells per mL and used directly in the cAMP assay as described.

5-HT$_7$ Receptor Affinity: Radioligand Binding Assay:

[$^3$H] 5-HT binding is performed using modifications of the assay conditions reported by Kahl et al. (*J. Biomol. Screen*, 2: 33-40 (1997), essentially as follows. Radioligand binding assays are conducted in 96-well microtiter plates, in a total volume of 125 μl containing the following reaction buffer: 50 mM Tris, 10 mM MgCl$_2$, 0.2 mM EDTA, 10 mM pargyline, 0.1% ascorbate, pH 7.4 at room temperature. Competition binding is conducted using eleven test compound concentrations ranging from 0.1 to 10,000 nM, in the presence of 1 nM [$^3$H]5-HT. Unlabeled 5-HT (10 μM) is used to define nonspecific binding. The binding reaction is initiated by addition of 0.15 μg of membrane homogenate (2.31 ng/μL, 65 μL per well) and 0.5 mg of scintillation proximity assay fluoromicrospheres. The reactions are incubated at room temperature for 3 hr. and then counted in a Trilux Microbeta™ scintillation counter to detect receptor-bound radioligand. Binding data is analyzed by computer-assisted 4 parameter fit analysis (ID Business Solutions Ltd, Guildford, Surrey, UK). IC$_{50}$ values are converted to K$_i$ values using the Cheng-Prusoff equation. *Biochem. Pharmacol.*, 22:3099-3108 (1973).

Exemplified compounds are tested essentially as described and found to have K$_i$ values ≦55 nM. The compounds of Examples 17 and 25 are tested essentially as described and found to have a K$_i$ values of about 33.5 nM and 19.4 nM, respectively.

Affinity for other serotonin receptor subtypes as well as for alpha 1 & 2 adrenergic receptors can readily be determined by modification of the above described radioligand receptor binding assay using membranes derived from cells stably expressing the desired receptor subtype including the 5-HT$_{1A}$, 5-HT$_{1B}$, and 5-HT$_{1D}$ subtypes, as well as the 5-HT$_{2A}$, 5-HT$_{2B}$, 5-HT$_{2C}$, 5-HT$_4$, 5-HT$_5$, and 5-HT$_6$ receptor subtypes. The selectivity ratio of K$_{i-x}$/K$_{i-5HT7}$, where K$_{i-x}$ is the K$_i$ for the receptor being compared, is indicative of the relative affinity of a compound for the 5-HT$_7$ receptor. Exemplified compounds are tested and found to have selectivity ratios against other serotonergic receptors of ≧9 and against andronergic receptors of >9. The compounds of Examples 17 and 25 are tested essentially as described and are found to have the following selectivity profiles:

| Receptor | Ex. 17 K$_i$ (nM) | Ex. 25 K$_i$ (nM) |
|---|---|---|
| 5-HT$_{1A}$ | 1500 | 2070 |
| 5-HT$_{1B}$ | >3580 | 3240 |
| 5-HT$_{1D}$ | >2320 | 1270 |
| 5-HT$_{2A}$ | >7470 | >7470 |
| 5-HT$_{2B}$ | >6810 | >6810 |
| 5-HT$_{2C}$ | >8360 | >8360 |
| 5-HT$_4$ | >6310 | >4120 |
| 5-HT$_5$ | >6710 | 3320 |
| 5-HT$_6$ | >5830 | >5830 |
| 5-HT$_7$ | 33.5 | 19.4 |
| alpha 1 adrenergic | >1770 | 2330 |
| alpha 2 adrenergic | >2430 | >5290 |

Functional Antagonist Assay: Measurement of cAMP Formation:

The 5-HT$_7$ receptor is functionally coupled to a G-protein as measured by the ability of serotonin and serotonergic drugs to stimulate cAMP production in CHO cells transfected with the 5-HT$_7$ receptor. (Ruat, et al., *Proceedings of the National Academy of Sciences (USA)*, 90:8547-8551, 1993.) Accordingly, functional receptor activity can be measured by measuring adenylate cyclase activity using a commercially available cell-based, homogeneous, time resolved fluorescence assay kit, as for example the kit produced by Cisbio-US, Inc. (Bedford, Mass.). Essentially, and using the protocol and reagents provided by the manufacturer, approximately 20,000 human 5-HT$_7$ receptor-expressing AV-12 cells (as described above) are used with test compound dose concentrations in the range described for the binding assay. EC-90 dose-response curves for 5-HT are measured in parallel to demonstrate competitive antagonism. A cAMP standard curve is also run in every experiment. After the assay plates are read in an Envision™ instrument (Perkin-Elmer, Wellesley Mass.), the data are normalized to the standard curve and converted to percent inhibition for data analysis as described above for the receptor binding assay results. The $K_b$ (nM) is calculated as a measure of the antagonist potency of the compound. Preferred compounds are those having percent inhibition>75%. Still other preferred compounds are those having $K_b$<50 nM. The compounds of Example 4 and 25 are tested essentially as described and are found to be full antagonists with $K_b$ values of about 24 nM (inhibition=about 128%) and 8.5 nM, respectively.

Animal Model of Dural Plasma Protein Extravasation (PPE).

The dural plasma protein extravasation model is an established model for migraine. The ability of a test compound to reduce extravasation of plasma proteins into the dura under assay conditions is considered indicative of the compound's ability to reduce or prevent the dural inflammation thought to be symptomatic of migraine. (see Johnson, K. W., et al., *Neuroreport*, 8 (1997) 2237-2240.)

To assay compounds for their ability to reduce or prevent dural plasma protein extravasation, male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagittal scalp incision, 2 pairs of bilateral holes are drilled through the skull (3.2 mm posterially, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

Test compound is administered intravenously (i.v.) to the femoral vein at a dosing volume of 1 mL/kg. Approximately 8 min. post injection, the animals are dosed with Fluorescein isothiocyanate-bovine serum albumin (FITC-BSA) (20 mg/kg, i.v.). The FITC-BSA functions as a marker for protein extravasation. Ten min. post-injection of the test compound, the left trigeminal ganglion is electrically stimulated for 5 min. at a current intensity of 1.0 mA (5 Hz, 5 msec pulse every 200 msec) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 min. post dosing, the animals are anesthetized and placed in the stereotaxic frame as described above. The animals are dosed with FITC-BSA (20 mg/kg, i.v.) at 58 min. post-p.o. dosing. Sixty min. post compound dosing, the animals are electrically stimulated as described above.

Five minutes following the termination of stimulation, the animals are killed by exsanguination with 40 mL of saline. The top of the skull is removed and the dural membrane samples are removed from both hemispheres, rinsed with water, and spread flat on microscopic slides. Once dried, the tissues are coverslipped with a 70% glycerol/water solution.

The amount of FITC-BSA for each sample is quantified with a fluorescence microscope (Zeiss) equipped with a grating monochromator, a spectrophotometer, and a computer driven stage. Fluorescence measurements are taken at 25 points in a 5×5 grid in 500 μm steps on each dural sample with an excitation wavelength of approximately 490 nm and emission intensity measured at approximately 535 nm. The mean and standard deviation of the 25 measurements are determined.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0.

Preferred compounds are those that effectively prevent extravasation. The compound of Example 25 is assayed essentially as described and is found to have an $ID_{100}$ of 1 mg/Kg, providing a ratio of about 1.1.

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, intranasal, transdermal, subcutaneous, intravenous, intramuscular, and pulmonary. Such pharmaceutical compositions and processes for preparing them are well known in the art. See, e.g., Remington: The Science and Practice of Pharmacy (University of the Sciences in Philadelphia, ed., $21^{st}$ ed., Lippincott Williams & Wilkins Co., 2005).

The compositions are preferably formulated in a unit dosage form, each dosage containing from about 0.1 to about 200 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds are generally effective over a wide dosage range. For example, dosages per day will normally fall within the range of about 0.01 to about 30 mg/kg, as for example within the range of about 0.1 to about 15 mg/kg/day, in single or divided dose. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the above lower limit may be adequate, while in other cases still larger doses may be used.

The type of formulation employed for the administration of the compounds employed in the methods of the present invention may be dictated by the particular compound employed, the type of pharmacokinetic profile desired from the selected route of administration, and the state of the patient.

We claim:

1. A compound of the formula:

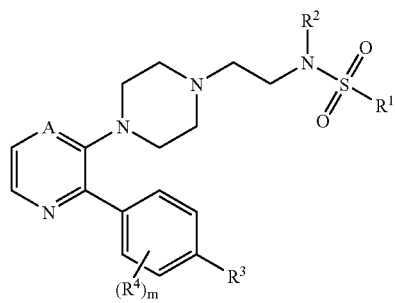

where:
- A is —N=,
- $R^1$ is selected from the group consisting of phenyl optionally substituted with methoxy or 1 to 3 independently selected chloro or fluoro substituents; pyrazol-4-yl optionally substituted with 1 to 3 methyl or ethyl groups; imidazolyl optionally substituted with 1 or 2 methyl or ethyl groups; pyridyl optionally substituted with fluoro or chloro; and thienyl;
- $R^2$ is hydrogen or methyl;
- m is 0, 1, or 2;
- $R^3$ is selected from the group consisting of hydrogen, fluoro, chloro, hydroxy, methoxy, hydroxymethyl, cyanomethyl, methoxymethyl, acetyl, methylcarbonylamino, methylcarbonylaminomethyl, pyrazol-1-ylmethyl, and triazolylmethyl, provided that when $R^3$ is hydrogen, m is not 0;
- each $R^4$ is independently selected from the group consisting of fluoro, chloro, methyl, and methoxy; or alternatively, two $R^4$ groups together with the phenyl to which they are attached join to form an indol-4-yl group;

or a pharmaceutically acceptable salt thereof.

2. A compound according to claim 1 wherein $R^1$ is phenyl optionally substituted with methoxy or 1 to 3 independently selected chloro or fluoro substituents; or a pharmaceutically acceptable salt thereof.

3. A compound according to claim 1 wherein $R^1$ is pyrazol-4-yl optionally substituted with 1 to 3 methyl or ethyl groups; or a pharmaceutically acceptable salt thereof.

4. A compound according to claim 1 wherein $R^1$ is imidazolyl optionally substituted with 1 or 2 $C_1$-$C_3$ methyl or ethyl; or a pharmaceutically acceptable salt thereof.

5. A compound according to claim 1 wherein $R^1$ is pyridyl optionally substituted with fluoro or chloro; or a pharmaceutically acceptable salt thereof.

6. A compound according to claim 1 wherein $R^1$ is thienyl; or a pharmaceutically acceptable salt thereof.

7. A compound according to claim 1 wherein $R^3$ is fluoro or methoxymethyl; or a pharmaceutically acceptable salt thereof.

8. A compound according to claim 1 which is 1-methyl-1H-pyrazole-4-sulfonic acid {2-[3'-(4-methoxymethyl-phenyl)-2,3,5,6-tetrahydro-[1,2']bipyrazinyl-4-yl]-ethyl}-methyl-amide or a pharmaceutically acceptable salt thereof.

9. A compound according to claim 1 which is 1-methyl-1H-pyrazole-4-sulfonic acid {2-[3'-(4-hydroxymethyl-phenyl)-2,3,5,6-tetrahydro-[1,2']bipyrazinyl-4-yl]-ethyl}-methyl-amide or a pharmaceutically acceptable salt thereof.

10. A pharmaceutical composition comprising a compound according to claim 1, or a pharmaceutically acceptable salt thereof, as an active ingredient in association with a pharmaceutically acceptable carrier, diluent or excipient.

11. A method for the treatment of migraine in humans, comprising administering to a human in need of such treatment an effective amount of a compound according to claim 1.

12. A pharmaceutical composition comprising a compound according to claim 8, or a pharmaceutically acceptable salt thereof, as an active ingredient in association with a pharmaceutically acceptable carrier, diluent or excipient.

13. A pharmaceutical composition comprising a compound according to claim 9, or a pharmaceutically acceptable salt thereof, as an active ingredient in association with a pharmaceutically acceptable carrier, diluent or excipient.

* * * * *